(12) United States Patent
Sterk

(10) Patent No.: US 8,703,996 B2
(45) Date of Patent: Apr. 22, 2014

(54) SHORT SYNTHESIS OF TOLTERODIN, INTERMEDIATES AND METABOLITES

(75) Inventor: Damjan Sterk, Ljubljana (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 0 days.

(21) Appl. No.: 13/582,947

(22) PCT Filed: Mar. 8, 2011

(86) PCT No.: PCT/EP2011/053465
§ 371 (c)(1),
(2), (4) Date: Nov. 7, 2012

(87) PCT Pub. No.: WO2011/110556
PCT Pub. Date: Sep. 15, 2011

(65) Prior Publication Data
US 2013/0197082 A1    Aug. 1, 2013

(30) Foreign Application Priority Data

Mar. 9, 2010    (EP) ..................................... 10155864

(51) Int. Cl.
*C07C 67/02*    (2006.01)
(52) U.S. Cl.
USPC .......................................... 560/255; 564/316
(58) Field of Classification Search
USPC .......................................... 564/316; 560/255
See application file for complete search history.

(56) References Cited

U.S. PATENT DOCUMENTS

| | | | | |
|---|---|---|---|---|
| 6,313,132 | B1 * | 11/2001 | Johansson et al. | ............. 514/277 |
| 2009/0214642 | A1 | 8/2009 | Legen et al. | |
| 2010/0234473 | A1 | 9/2010 | Fischer | |

FOREIGN PATENT DOCUMENTS

| | | |
|---|---|---|
| EP | 1 839 649 A1 | 10/2007 |
| EP | 2 281 801 A1 | 2/2011 |
| WO | WO 98/43942 A1 | 10/1998 |
| WO | WO 2005/012227 A2 | 2/2005 |
| WO | WO 2007/147547 A1 | 12/2007 |

OTHER PUBLICATIONS

Gopalakrishnan et al., "Kinetic and mechanistic Studies of the N-Bromosuccinimide-Promoted Oxidative Decarboxylation of Glycine, DL-Alanine and DL-Valine", J. Org. Chem., vol. 50, 1985, pp. 1206-1212.
Husman et al., " Chemical Insights in the Concept of Hybrid Drugs: The Antitumor Effect of Nitric Oxide-Donating Aspirin Involves A Quinone Methide but Not Nitric Oxide nor Aspirin", J. Med. Chem., vol. 50, 2007, pp. 2424-2431.

* cited by examiner

*Primary Examiner* — Rei-tsang Shiao
(74) *Attorney, Agent, or Firm* — Arent Fox LLP

(57) ABSTRACT

A process is described for the preparation of intermediates which can be used for preparation of agents for urinary incontinence therapy, specifically to 2-(3-(diisopropylamino)-1-phenylpropyl)-4-(hydroxymethyl)phenol and its prodrugs.

7 Claims, No Drawings

SHORT SYNTHESIS OF TOLTERODIN, INTERMEDIATES AND METABOLITES

CROSS-REFERENCE TO RELATED APPLICATION

This application is a National Stage entry of International Application No. PCT/EP2011/053465, filed Mar. 8, 2011, which claims priority to European Application No. 10155864.1, filed Mar. 9, 2010, the entire specifications, claims and drawings of which are incorporated herewith by reference.

FIELD OF THE INVENTION

The present invention relates to a process for the preparation of common intermediates which can be used for preparation of agents for urinary incontinence therapy, specifically to 2-(3-(diisopropylamino)-1-phenylpropyl)-4-(hydroxymethyl)phenol and its prodrugs.

BACKGROUND OF THE INVENTION

Tolterodine (3-(2-hydroxy-5-methylphenyl)-N,N-diisopropyl-3-phenylpropylamine) is a muscarinic receptor antagonist for the treatment of overactive bladder including urinary incontinence. In the body it is converted to a hydroxy metabolite 2-(3-(diisopropylamino)-1-phenylpropyl)-4-(hydroxymethyl)phenol (hydroxytolterodine, HT), which is also an active molecule.

Hydroxytolterodine (HT) was firstly prepared in WO 94/011337 in a synthesis, which is extremely long. Similar approach was repeated in WO 99/058478 and optimised in WO 07/138,440, WO 07/144,097 and WO 07/144,091. Described synthetic variations involve synthesis via bromo substituted lactone derivative (the bromo process) in 9 to 11 steps, in which some steps include reagents, unwanted in a routine industrial process such as Grignard reagents and aluminium hydrides.

The bromo process is shown in three partial schemes.

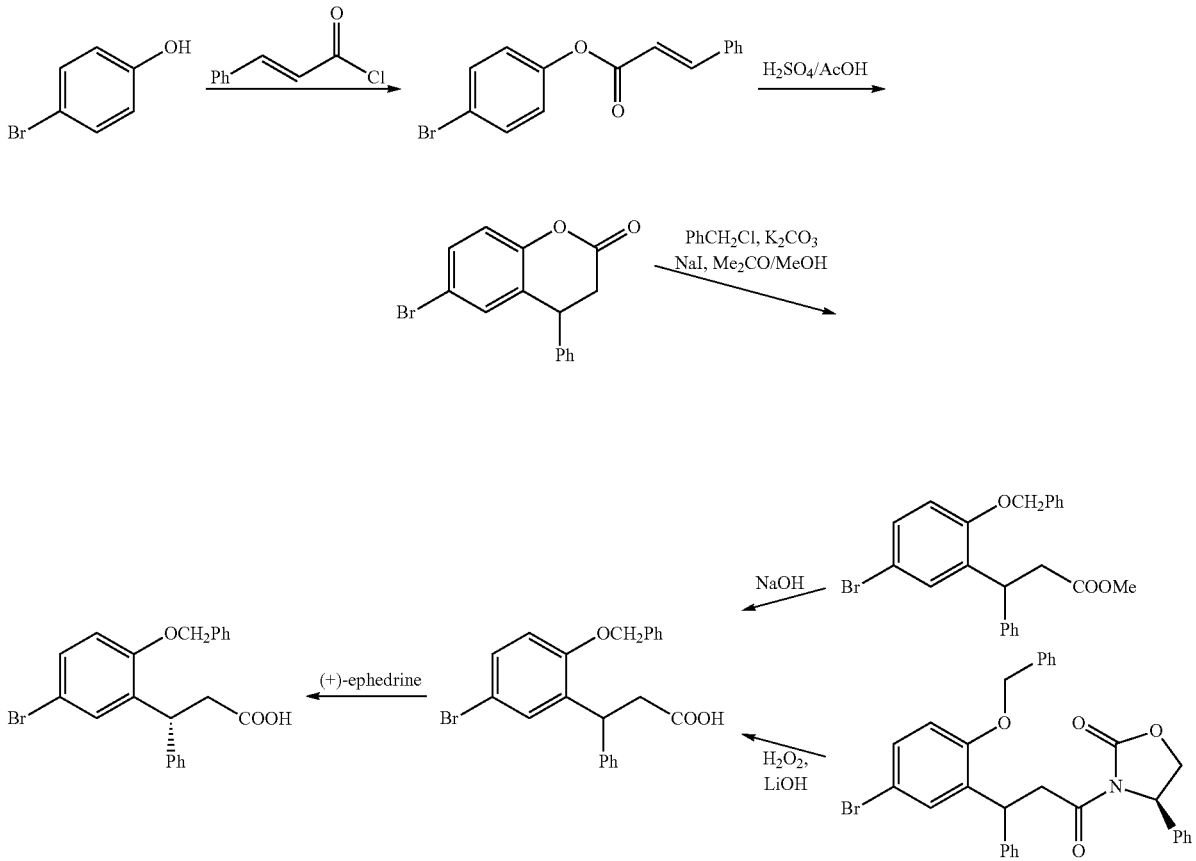

-continued
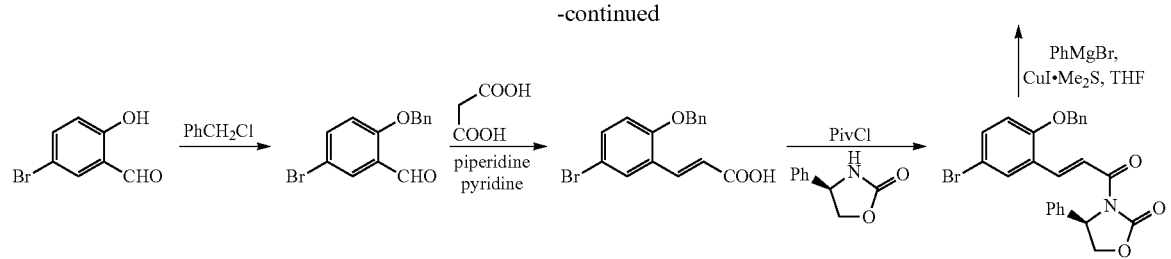

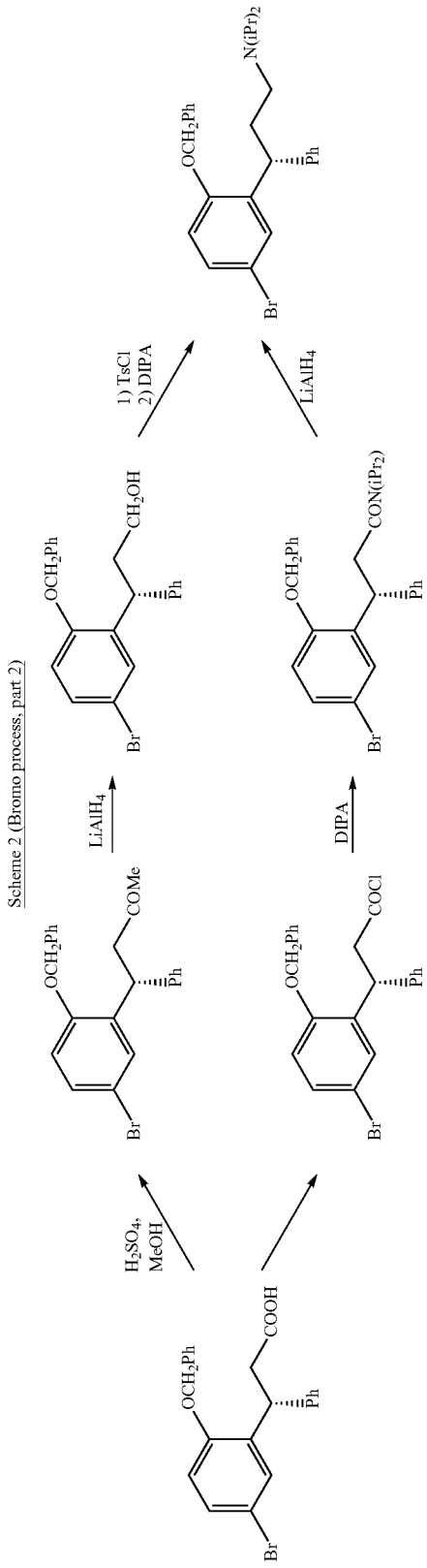

Scheme 3 (Bromo process, part 3)

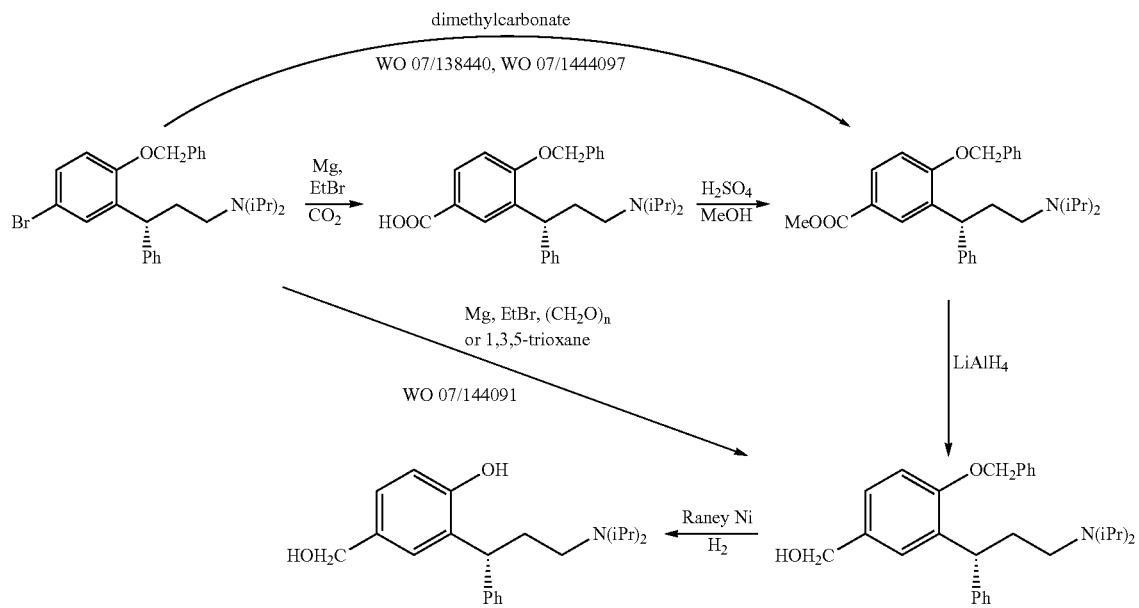

Several approaches how to simplify the first published process were later developed. An approach via hydrocoumarines (the lactone route), known from preparations of tolterodine was applied to intermediates with different para phenol substituents. The approaches are summarized in Scheme 4 in which transformations shown by arrows can be multistep and the preparations differ each to each by different para phenol substituents R(COOR', COOH, halo, Me, CH$_2$OH), using or omitting protective groups, and in which step the reduction is carried out. The preparations are described at least but not limited in WO 89/006644, WO 01/096279, Org. Lett. 7, 2285 (2005), WO 07/144,097.

The shortest modification of above described lactone process is described in WO 07/138,440. In this process the lactol is formed in one step by cinnamaldehyde. The lactol is then transformed further into HT by reaction with diisopropylamine and hydrogen gas in the presence of Pd/C. The formation of lactol suffers of low yield and by-products so it must be accomplished by use of amines and isolation of intermediate aminal ethers what makes process longer. Major issues with this synthesis are a use of heavy metals and of hydrogen gas. Synthesis is shown in Scheme 5.

Scheme 4

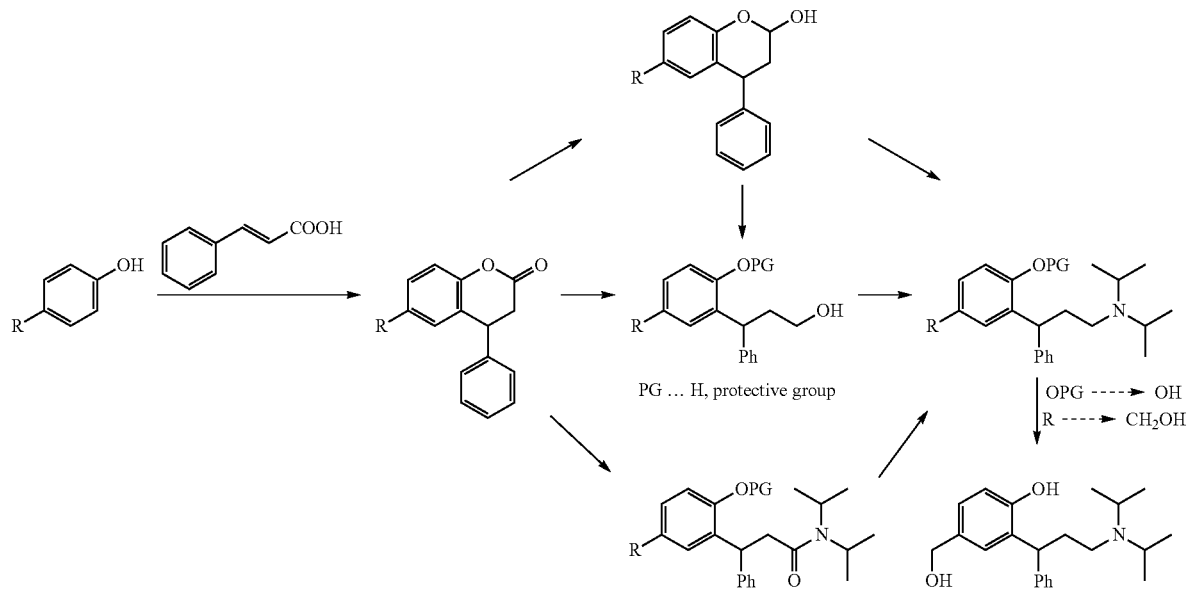

Scheme 5

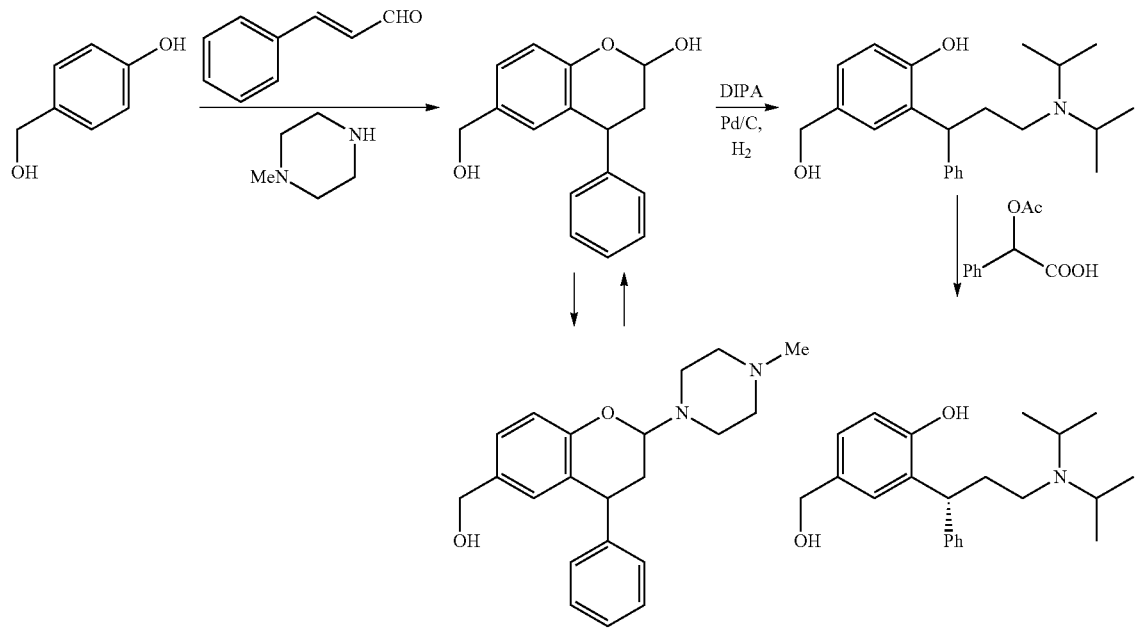

Some other synthetic routes use reagents that are less common for industrial purposes. Such routes are described in WO 94/011337 and WO 02/004399. The former involves a Heck reaction step, which is followed by organolithium coupling in the presence of copper salt and a reduction step (the Heck-cuprate process, Scheme 6).

The latter describes a reaction with phenylacetylene (the phenylacetylene route, Scheme 7) in the presence of $SnCl_4$ and a reaction with carbon monoxide and diisopropylamine in the presence of BINAP/Pd catalyst. Both procedures use hydrogen gas, heavy metals, and strong reducing agents, toxic and potentially hazardous reagents.

Scheme 6 (Heck process)

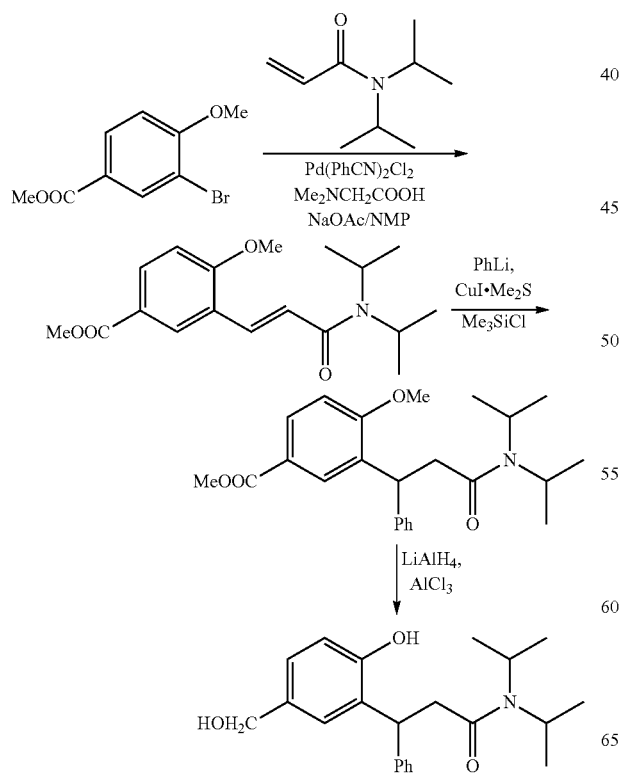

Scheme 7

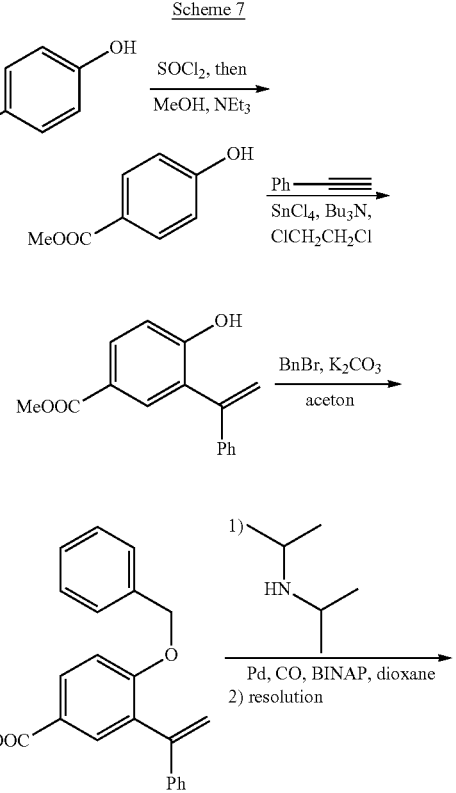

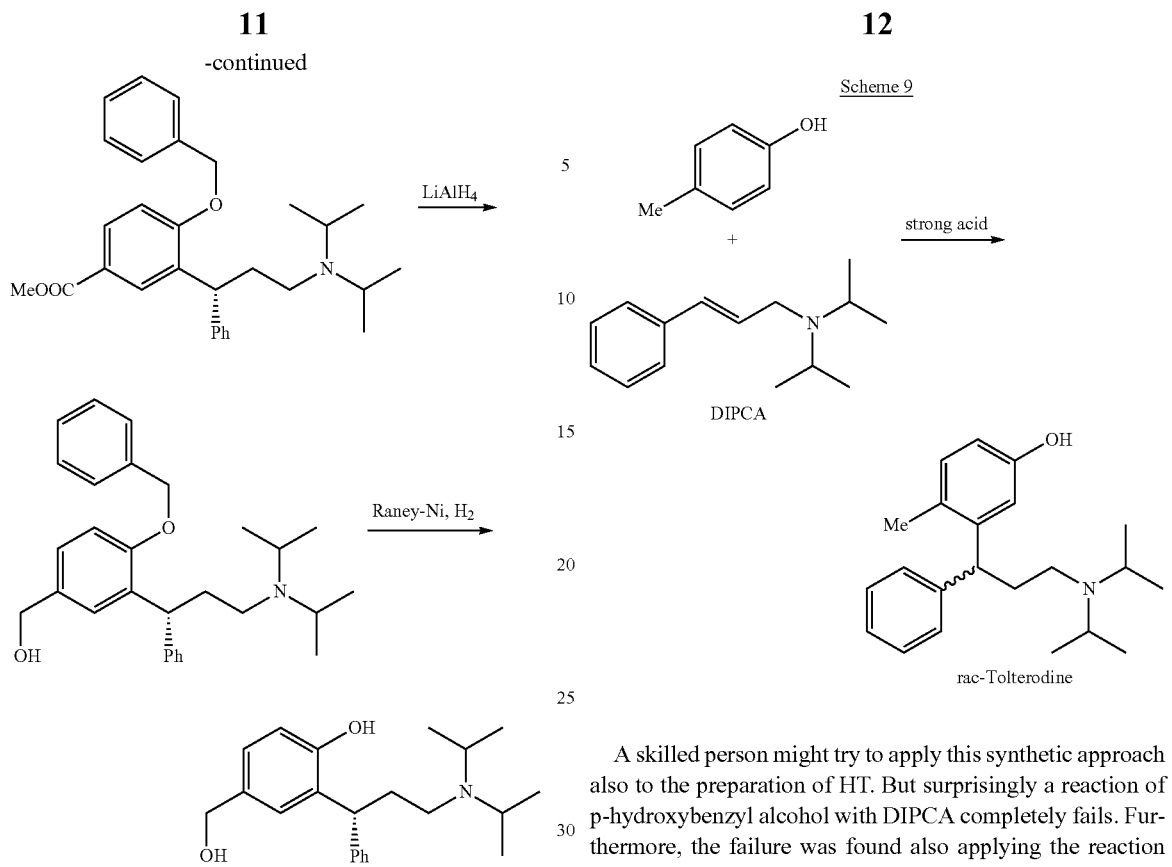

Another synthesis is described in WO 05/012227. HT is prepared by oxidation of tolterodine. An oxidation of toluenic methyl group is not easy and demands protection of phenolic hydroxy group what essentially prolongs the synthesis of HT.

A skilled person might try to apply this synthetic approach also to the preparation of HT. But surprisingly a reaction of p-hydroxybenzyl alcohol with DIPCA completely fails. Furthermore, the failure was found also applying the reaction with phenols, para substituted with groups, convertible to hydroxymethyl group, such as p-hydroxybenzoic acid, p-hydroxybenzoic esters, p-cyanophenol and p-hydroxybenzaldehyde and also with their corresponding O-protected analogues. The reaction could be applied only on halo derivatives

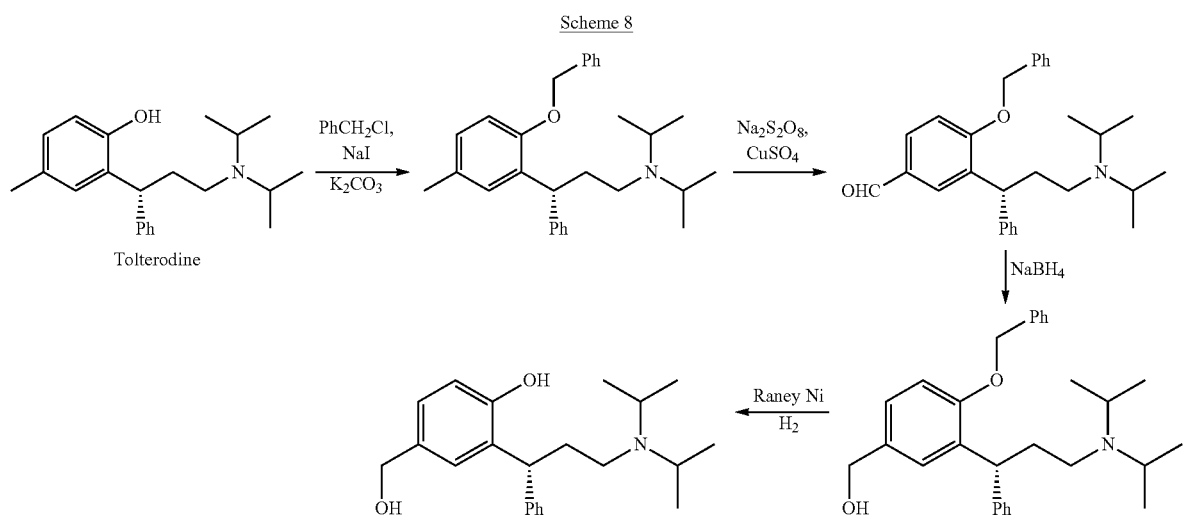

The shortest synthesis of tolterodine is described in WO 07/017,544 and WO 07/147,547 and is shown in Scheme 9. Excess of p-cresol reacted in a neat or a concentrated strong acid such as methansulphonic, hydrobromic, sulfuric, perchloric or p-toluenesulfonic acid with N,N-diisopropyl-3-phenylprop-2-en-1-amine (N,N-diisopropyl cinnamylamine, DIPCA) to give tolterodine in only one step.

but a transformation of halo to hydroxymethyl group needs Grignard reaction and a protection of phenolic group as shown in Schemes 1-3, that considerably prolongs the synthesis.

Possible transformations of some groups to the hydroxymethyl group of HT are listed below and are summarized in Scheme 10.

| | | |
|---|---|---|
| a | halogen | Grignard reaction, protection of phenol, reductions |
| b | alkoxycarbonyl | protection of phenol, anhydrous reductions |
| c | carboxy | protection of phenol, anhydrous reductions, optionally transformation to esters |
| d | cyano | double reduction or hydrolysis + reduction |
| e | formyl | non-anhydrous one step reduction |

Scheme 10

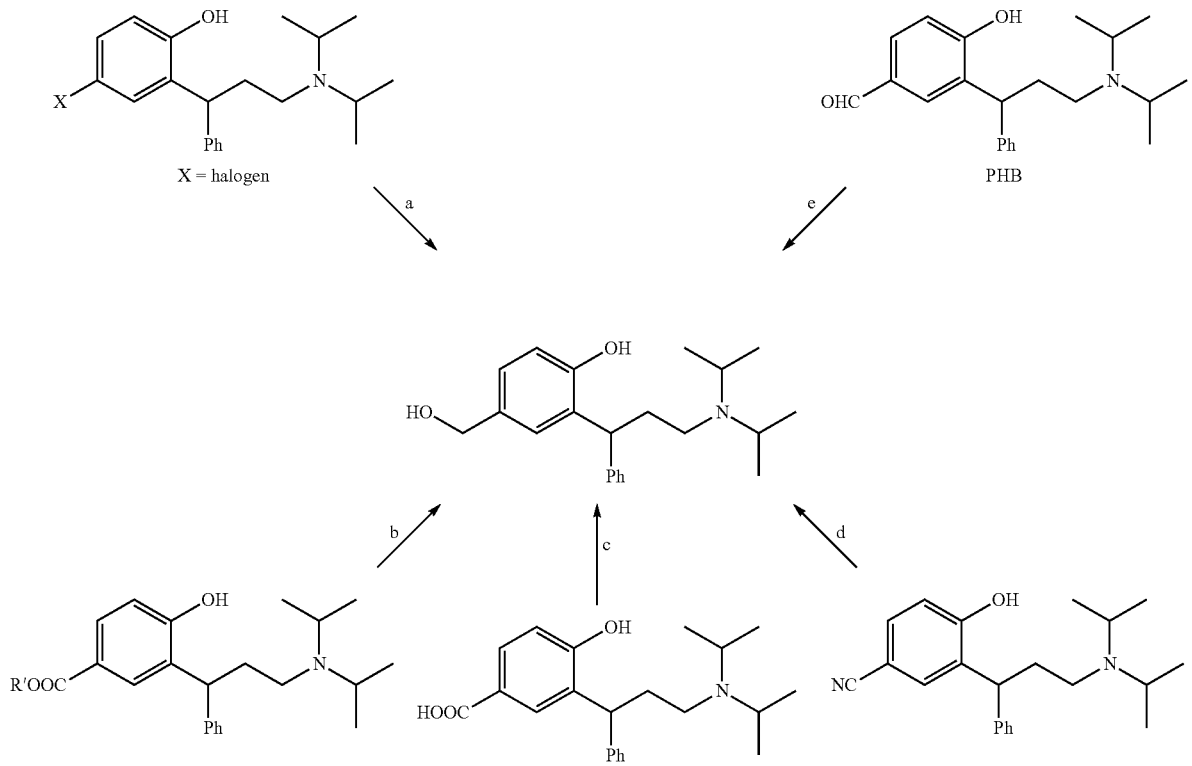

A skilled person might try to synthesize HT by way of reduction of 3-(5-formyl-2-hydroxyphenyl)-N,N-diisopropyl-3-phenylpropylamine (PHB). The synthesis of PHB by reacting DIPCA and p-hydroxybenzaldehyde in the presence of a strong acid has been disclosed in WO 07/147,547. However, the disadvantages of said synthesis of PHB are very low yields (e.g. 8%).

Therefore, there is still a need for a short synthesis of 3-(5-formyl-2-hydroxyphenyl)-N,N-diisopropyl-3-phenyl-propylamine (PHB) with higher yields for an efficient synthesis of hydroxytolterodine (HT).

SUMMARY OF THE INVENTION

The object of the present invention is to provide an industrially applicable, economical and acceptable process for obtaining key intermediates useful for synthesizing anticholinergic agents belonging to the class of 3,3-diphenylpropylamines, in particular for preparing hydroxytolterodine (HT), tolderodine or fesoterodine, respectively from readily available and optionally cheap and commercial starting compounds.

Aspects, advantageous features and preferred embodiments of the present invention summarized in the following items, respectively alone or in combination, contribute to solving this and other objects of the invention:

(1) A process of preparing a compound of formula D or a salt thereof:

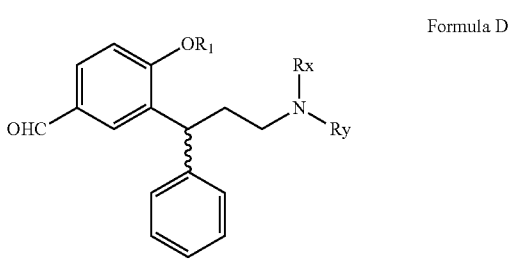

Formula D wherein $R_1$ is selected from H, $C_1$-$C_6$ alkyl, aryl substituted $C_1$-$C_2$ alkyl, $C_1$-$C_4$-alkyl substituted silyl, Rx is selected from H and $C_1$-$C_3$ alkyl; and Ry is selected from $C_1$-$C_3$ alkyl, wherein preferably Rx and Ry is isopropyl, comprising (a) reacting 3-phenylprop-2-en-1-amine of formula B or a salt thereof, wherein Rx and Ry are defined as above

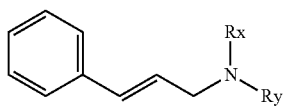

Formula B with hydroxyphenylglycine or a derivative thereof denoted by formula A

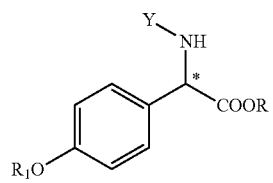

Formula A in which * denotes chiral C atom, $R_1$ is same as above, R is hydrogen, $C_1$-$C_6$ alkyl or aryl-$C_1$-$C_4$-alkyl and Y is hydrogen or COR', in which R' is selected from the group consisting of $C_1$-$C_4$ alkyl, $C_1$-$C_4$ alkoxy, benzyloxy, p-substituted benzyloxy and fluorenyloxy, in the presence of an acid, (b) optionally removing R and Y, if different from H, and
(c) oxidative decarboxylation in the presence of an oxidizing reagent.

(2) A process of preparing a 3-(5-formyl-2-hydroxyphenyl)-3-phenylpropylamine compound of formula D' or a salt thereof:

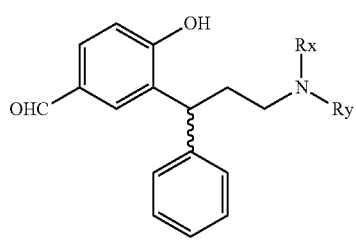

Formula D' wherein Rx is selected from H and $C_1$-$C_3$ alkyl; and Ry is selected from $C_1$-$C_3$ alkyl, wherein preferably Rx and Ry is isopropyl, comprising (a) reacting 3-phenylprop-2-en-1-amine of formula B or a salt thereof, wherein Rx and Ry are defined as above

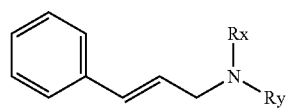

Formula B with hydroxyphenylglycine or a derivative thereof denoted by formula A'

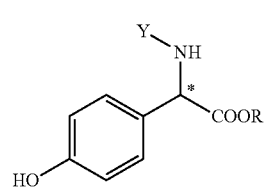

Formula A' in which * denotes chiral C atom, R is hydrogen, $C_1$-$C_6$ alkyl or aryl-$C_1$-$C_4$-alkyl and Y is hydrogen or COR', in which R' is selected from the group consisting of $C_1$-$C_4$ alkyl, $C_1$-$C_4$ alkoxy, benzyloxy, p-substituted benzyloxy and fluorenyloxy, in the presence of an acid, (b) optionally removing R and Y, if different from H, and
(c) oxidative decarboxylation in the presence of an oxidizing reagent.

In the preferred embodiment Rx and Ry is isopropyl.

(3) The process according to item (1) or (2), wherein hydroxyphenylglycine is subjected to reaction in step (a).

(4) The process according to items (1) to (3), wherein steps (a) and (b) proceed in a one pot reaction.

In such a preferred embodiment, it is possible to efficiently carry out steps (a) and (b) without a need to isolate any intermediate compound generated during the reactions.

(5) The process according to any one of the preceding items, wherein the acid in step (a) is selected from inorganic acids and organic sulfonic acids, preferably selected from sulfuric acid, perchloric acid, $C_1$-$C_6$ alkanesulfonic acids, fluorinated $C_1$-$C_6$ alkanesulfonic acids, arenesulfonic acids, more preferably selected from methanesulfonic and sulfuric acid.

(6) The process according to any one of the preceding items, wherein the acid is diluted with water and/or with aliphatic acid, preferably the water content is less than 50% (w/w), more preferably less than 30% (w/w).

(7) The process according to any one of the preceding items, wherein no organic solvent is contained in or added to the reaction solution for step (a).

(8) The process according to any one of the preceding items, wherein before step (c), the acid reaction solution of step (a) is adjusted to a pH in the range from 5 to 9, preferably in the range from 6.5 to 7.5, then a water immiscible solvent is added, and then step (c) is carried out.

(9) The process according to item (8), wherein the water immiscible solvent is selected from ethers or esters, more preferably from acetic esters.

(10) The process according to any one of the preceding items, wherein step (c) is carried out by any one of
  (i) using a transamination reagent selected from reactive aldehydes and ketones;
  (ii) using air oxygen in the presence of a radical catalyst;
  (iii) using inorganic oxidants selected form salts of metal cations in relatively high oxidation states, and anions in relatively high oxidation states.

(11) The process according to item (10), wherein oxidation is carried out
  according to (i) and the used transamination reagent is selected from sugars, preferably glucose; quinones, preferably benzoquinone; and α-keto substituted carbonyl compounds, in particular from glyoxalic and pyruvic acids and their salts, esters and aldehydes.

(12) The process according to item (11), wherein α-keto substituted carbonyl compounds is used, most preferably using methylglyoxal.

(13) The process according to item (10), wherein oxidation is carried out
  according to (ii) and the used radical catalyst is selected from organic compounds, preferably ascorbic acid or isatin, and transition metal cations, preferably copper (II) salts.

(14) The process according to item (10), wherein oxidation is carried out according to (iii) and the used metal cation is $Fe^{3+}$, or the used highly oxidized anion is selected from nitrites and persulfates.

(15) The process according to item (14), using an inorganic persulfate, preferably selected from alkali metal peroxodisulfates, or using peroxodisulfate species prepared in situ from corresponding sulfuric salts and hydrogen peroxide.

(16) The process for the preparation of a compound of Formula E or a salt thereof according to any of the previous items

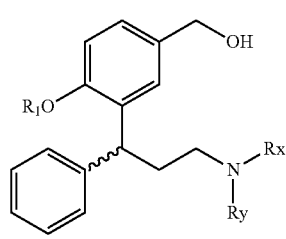

Formula E in which $R_1$ is H, $C_1$-$C_6$ alkyl, aryl substituted $C_1$-$C_2$ alkyl, $C_1$-$C_4$-alkyl substituted silyl, Rx is selected from H and $C_1$-$C_3$ alkyl; and Ry is selected from $C_1$-$C_3$ alkyl ($R_1$ is preferably H, and independently Rx and Ry are preferably isopropyl), the process comprising: carrying out a process according to any one of items (1) to (15) to provide a compound of formula D

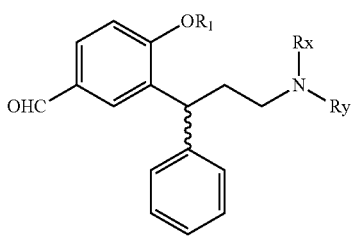

Formula D wherein $R_1$, Rx and Ry are same as above, and selective reduction of formyl group, preferably by borohydrides to give the compound of formula E; optionally further comprising forming a salt of the compound of formula E.

(17) The process according to item (16), further comprising subjecting the compound of formula E, in which R1 is hydrogen to define a phenolic hydroxy group, to a reaction for acylation of the phenolic hydroxy group, and optionally forming a salt of the acylated product.

(18) The process of preparing hydroxytolterodine or its salts, comprising:
preparing 3-(5-formyl-2-hydroxyphenyl)-N,N-diisopropyl-3-phenylpropylamine according to any one of items (1) to (16),
carrying out a reduction step to obtain hydroxytolterodine (HT),

(19) The process according to item (18), wherein the reduction step uses aluminumhydride or borohydride as reducing agent.

(20) The process according to item (18) or (19), wherein reduction step uses borohydride in an alcohol, preferably in methanol.

(21) The process according to any one of items (18) to (20), wherein after reduction step to obtain hydroxytolterodine (HT), further comprising separating from the product (R)-HT, or converting HT into (R)-HT.

(22) The process according to any one of items (18) to (21), wherein after obtaining hydroxytolterodine (HT) or (R)-HT, further comprising a step of forming a salt of (HT) or (R)-HT.

(23) The process according to item (21) or (22), wherein
(R)-HT is separated from the product by chiral column chromatography, or the obtained hydroxytolterodine (HT) is converted into (R)-HT via fractional crystallization with a chiral organic acid, preferably with chiral 2-acetoxy(phenyl)acetic acid.

(24) The process according to items (1) to (16) further comprising the preparation of the compound of Formula G or a salt thereof

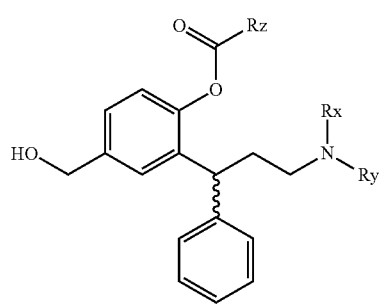

Formula G wherein Rx is selected from H and $C_1$-$C_3$ alkyl; Ry is selected from $C_1$-$C_3$ alkyl, and Rz is selected from H, $C_1$-$C_8$-alkyl or phenyl
in which the compound of formula D'

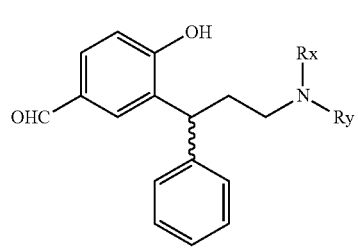

Formula D' in which Rx and Ry are same as above
is subjected to acylation
to give an intermediate of Formula F

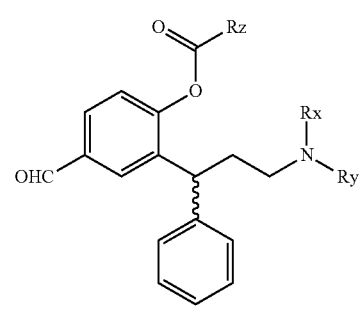

Formula F wherein Rx, Ry and Rz are the same as above, and
selective reduction of formyl group, preferably by borohydrides to give the compound of formula G; optionally further comprising forming a salt of the compound of formula G.

(25) A process of preparing acylated hydroxytolterodine or its salts, comprising:
preparing hydroxytolterodine (HT) or chiral (R)-HT or a salt thereof according to any one of items (18) to (23), and
carrying out acylation of the phenolic hydroxy group of HT or chiral (R)-HT by an alkanoic acid having straight chain or branched chain alkane residue,
and optionally converting the acylated hydroxytolterodine into a salt thereof.

(26) The process according to item (25), wherein the acylation is carried out by a reactive alkanoic acid derivative selected from acid chlorides and acid anhydrides.

(27) The process according to item (25) or (26) for preparing fesoterodine or its salts, wherein the acylation is carried out by isobutyryl chloride or isobutyric anhydride to obtain fesoterodine, and optionally converting fesoterodine into a salt thereof, preferably into fumarate salt.

(28) A process of preparing fesoterodine or a salt thereof, comprising the steps of:
(a) reacting N,N-diisopropyl-3-phenylprop-2-en-1-amine with hydroxyphenylglycine or a derivative thereof denoted by formula A'

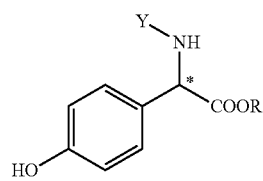

Formula A' in which * denotes chiral C atom, R is hydrogen, $C_1$-$C_6$ alkyl or aryl-$C_1$-$C_4$-alkyl and Y is hydrogen or COR', in which R' is selected from the group consisting of $C_1$-$C_4$ alkyl, $C_1$-$C_4$ alkoxy, benzyloxy, p-substituted benzyloxy and fluorenyloxy,
in the presence of an acid;
(b) optionally removing R and Y, if different from H;
(c) oxidative decarboxylation in the presence of an oxidizing reagent to obtain 3-(5-formyl-2-hydroxyphenyl)-N,N-diisopropyl-3-phenylpropylamine;
(d) reducing the formed 3-(5-formyl-2-hydroxyphenyl)-N,N-diisopropyl-3-phenylpropylamine to obtain hydroxytolterodine (HT);
(e) converting the obtained HT into (R)-HT; and
(f) carrying out acylation of the phenolic hydroxy group of (R)-HT obtained in step (d) by isobutyryl chloride or isobutyric anhydride to obtain fesoterodine,
(g) optionally converting fesoterodine into a salt thereof, preferably into fumarate salt; or
wherein steps (d)-(f) are replaced by the steps of:
(d') carrying out acylation of the phenolic hydroxy group of 3-(5-formyl-2-hydroxyphenyl)-N,N-diisopropyl-3-phenylpropylamine obtained in step (c) by isobutyryl chloride or isobutyric anhydride,
(e') followed by selective reduction of formyl group;
wherein optionally any of the compounds of the steps (d)-(g) or (d')-(e') are separated into enantiomers, preferably isolating the respective (R)-enantiomer.

(29) The process according to item (28), wherein
conversion of the obtained HT into (R)-HT in step (d) via fractional crystallization with a chiral organic acid, preferably with (R)-acetoxy(phenyl)acetic acid.

(30) The process according to items (28) or (29), wherein the acylation of the phenolic hydroxy group (f) is carried out after the step (b).

(31) A compound of formula C or a salt thereof.

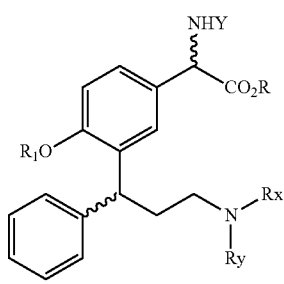

Formula C in which $R_1$ is H, $C_1$-$C_6$ alkyl, aryl substituted $C_1$-$C_2$ alkyl, $C_1$-$C_4$-alkyl substituted silyl, R is hydrogen, $C_1$-$C_6$ alkyl or aryl-$C_1$-$C_4$-alkyl and Y is hydrogen or COR', in which R' is selected from the group consisting of $C_1$-$C_4$ alkyl, $C_1$-$C_4$ alkoxy, benzyloxy, p-substituted benzyloxy and fluorenyloxy, Rx is selected from H and $C_1$-$C_3$ alkyl; and Ry is selected from $C_1$-$C_3$ alkyl.

In a preferred embodiment R, $R_1$, and Y are H, and independently therefrom Rx and Ry preferably are isopropyl.

(32) A compound of formula F or a salt thereof

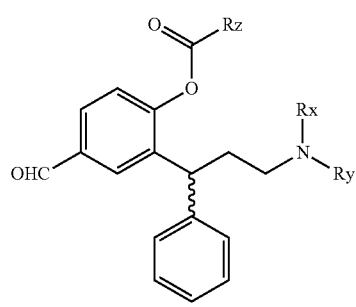

Formula F in which Rx is selected from H and $C_1$-$C_3$ alkyl; Ry is selected from $C_1$-$C_3$ alkyl, and Rz is selected from H, $C_1$-$C_8$-alkyl or phenyl;

(33) The compound according to item (32) wherein Rx, Ry and Rz are isopropyl.

(34) Use of the compounds as set forth in anyone of items (31) to (33) in a process of preparing a medicament, preferably for preparing an anticholinergic for treatment of urinary incontinence or overactive bladder.

(35) Use of the compound defined in anyone of items (31) to (33) for preparing hydroxytolterodine, tolterodine or fesoterodine, optionally in an enantiomeric pure form, and optionally a salt thereof.

(36) The use according to item (34) or (35), wherein hydroxytolterodine, tolterodine or fesoterodine is prepared in enantiomeric pure form, preferably in its (R)-configuration.

(37) A process for making a pharmaceutical composition comprising hydroxytolterodine, tolterodine or fesoterodine or a salt thereof as active pharmaceutical ingredient, comprising
providing hydroxytolterodine, tolterodine or fesoterodine or a salt thereof as active pharmaceutical ingredient by involving a process according to any one of items (18) to (30) or a use according to any one of items (34) to (36), and
formulating said active pharmaceutical ingredient with a pharmaceutically acceptable carrier to prepare the pharmaceutical composition.

DETAILED DESCRIPTION OF THE INVENTION

The invention relates to a synthesis of a compound of formula D or a salt thereof:

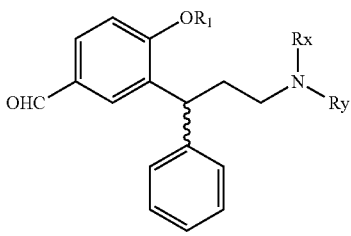

Formula D wherein $R_1$ is selected from H, $C_1$-$C_6$ alkyl, aryl substituted $C_1$-$C_2$ alkyl, $C_1$-$C_4$-alkyl substituted silyl, Rx is selected from H and $C_1$-$C_3$ alkyl; and Ry is selected from $C_1$-$C_3$ alkyl, preferably Rx and Ry is isopropyl, comprising
reacting a 3-phenylprop-2-en-1-amine of formula B or a salt thereof, wherein Rx and Ry are as defined above

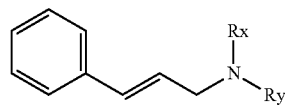

Formula B with hydroxyphenylglycine or a derivative thereof denoted by formula A

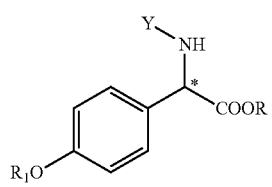

Formula A in which * denotes chiral C atom, $R_1$ is selected from H, $C_1$-$C_6$ alkyl, aryl substituted $C_1$-$C_2$ alkyl, $C_1$-$C_4$-alkyl substituted silyl, R is hydrogen, $C_1$-$C_6$ alkyl or aryl-$C_1$-$C_4$-alkyl and Y is hydrogen or COR' in which R' is selected from the group consisting of $C_1$-$C_4$ alkyl, $C_1$-$C_4$ alkoxy, benzyloxy, p-substituted benzyloxy and fluorenyloxy, preferably 2-amino-2-(4-hydroxyphenyl)acetic acid (hydroxyphenylglycine), in the presence of an acid, followed by oxidative decarboxylation in the presence of oxidizing reagents to give corresponding aldehyde of formula D.

In a preferred example of formula D, in which R, $R_1$, Y are H, and Rx, Ry are isopropyl the compound 3-(5-formyl-2-hydroxyphenyl)-N,N-diisopropyl-3-phenylpropylamine (PHB) is prepared from commercially available p-hydroxyphenylglycine and N,N-diisopropyl-3-phenylprop-2-en-1-amine (DIPCA). Surprisingly, it has been found that the yield of PHB by the reaction of DIPCA and p-hydroxyphenylglycine was higher than 20%, preferably higher than 30%. Due to the presence of the chiral C atom, the compound of formula A may be in (R)- or in (S)-configuration, or may be a mixture thereof. The conversion of the formyl group in the obtained PHB, which is provided for by the key synthesis step of the invention, is a very easy and efficient one for industrial purposes. For example and preferably, the aldehyde PHB can then be converted to hydroxytolterodine (HT) in a reduction step, and can preferably further be converted to chiral (R)-HT, further optionally converting HT or (R)-HT to salts thereof. Beneficially, conversion to chiral (R)-HT can be carried out with a process involving only one chemical step and one chiral separation step.

In one embodiment, an efficient synthesis of 3-(5-formyl-2-hydroxyphenyl)-N,N-diisopropyl-3-phenylpropylamine (PHB) is provided to obtain a key intermediate for the synthesis of HT or salts thereof. HT can be used as an efficient inhibitor of muscarinic inhibitors, and preferably it can be further modified to obtain further useful therapeutic agents. For example it can be acylated to produce prodrugs for treatment of urinary incontinency.

In particular, the invention relates to an embodiment wherein PHB, suitably via HT, is finally converted to fesoterodine or a salt thereof. Conversion can be carried out in only 3 steps using known protocols. These steps preferably include reduction using sodium borohydride, resolution of the product to (R)-isomer via diastereomeric salt formation with (R)-2-acetoxy(phenyl)acetic acid and subsequent esterification to fesoterodine. Fesoterodine can finally be converted into its salt, preferably into its fumarate salt by reaction with fumaric acid.

In a preferred embodiment of the invention, 3-(3-(diisopropylamino)-1-phenylpropyl)-4-hydroxybenzaldehyde (PHB) is synthesized comprising a reaction of 2-amino-2-(4-hydroxyphenyl)acetic acid (hydroxyphenylglycine) with N,N-diisopropyl-3-phenylprop-2-en-1-amine (DIPCA) in the presence of an acid, preferably at 80-150° C., to give 2-amino-2-(3-(3-(diisopropylamino)-1-phenylpropyl)-4-hydroxyphenyl)acetic acid (HFG), and a further reaction with a suitable oxidant, preferably in water at 30-105° C., to give PHB. Intermediate compound HFG can be isolated. But advantageously and preferably, the synthesis from DIPCA to PHB can be carried out in one pot, without intermediate isolation of HFG.

The procedure is schematically shown in the upper row of Scheme 11.

Scheme 11

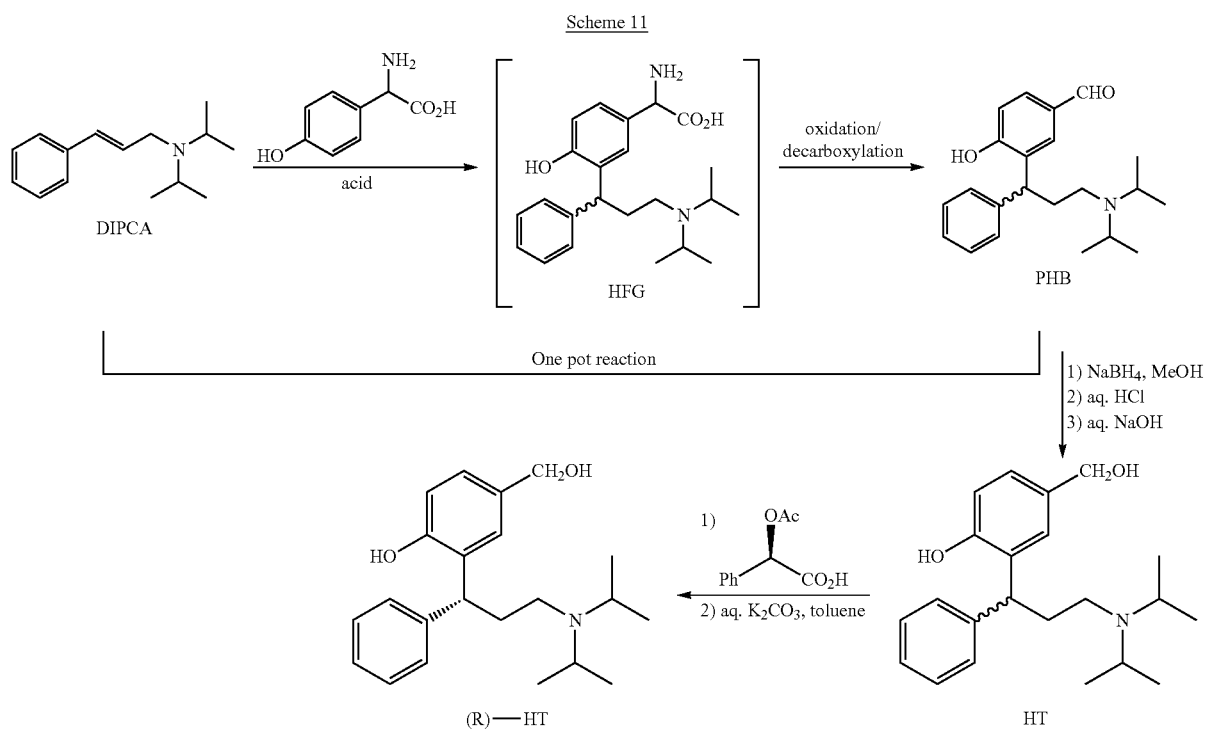

The procedure of Scheme 11 is a special, but not limited example of a more general process for preparation of compounds of formula E

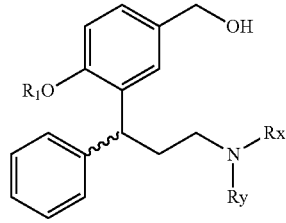

Formula E in which $R_1$ is H, $C_1$-$C_6$ alkyl, aryl substituted $C_1$-$C_2$ alkyl, $C_1$-$C_4$-alkyl substituted silyl, Rx is selected from H and $C_1$-$C_3$ alkyl; and Ry is selected from $C_1$-$C_3$ alkyl (preferably Rx and Ry is isopropyl)

Starting DIPCA can be prepared from cinnamyl chloride according to known procedure of WO 07/147,547 or from other cinnamyl derivatives like cinnamaldehyde or cinnamyl alcohol by methods known to a skilled person. Analogously other N-substituted cinnamamines are prepared.

Hydroxyphenylglycine is a cheap, commercially available starting material, known and used in production of semisynthetic beta-lactame antibiotics.

In a preferred embodiment, DIPCA is reacted with 0.9 to 2, more preferably with 1-1.4 molar equivalents of hydroxyphenylglycine compound of formula A as defined above, preferably Formula A in which C* has (R) or (S) configuration or a mixture thereof, $R_1$ is H, $C_1$-$C_6$ alkyl, aryl substituted $C_1$-$C_2$ alkyl, $C_1$-$C_4$-alkyl substituted silyl, R is hydrogen, $C_1$-$C_6$ alkyl or aryl-$C_1$-$C_4$-alkyl and Y is hydrogen or COR' in which R' is $C_1$-$C_4$ alkyl, $C_1$-$C_4$ alkoxy or benzyloxy, p-substituted benzyloxy, fluorenyloxy in a concentrated strong acid. Preferably R, $R_1$ and Y are H. The strong acid is selected from inorganic acids such as sulfuric and perchloric acid or organic sulfonic acids, such as $C_1$-$C_6$ alkanesulfonic acids, fluorinated $C_1$-$C_6$ alkanesulfonic acids, arenesulfonic acids, preferably the strong acid are selected from methanesulfonic and sulfuric acid. The strong acid is optionally diluted with water in preferably less than 50% (w/w), most preferably less than 30% (w/w) and/or with aliphatic acid, such as acetic acid. The reaction is carried out at 50-200° C., preferably at 80-150° C., most preferably at 110-130° C. for 2-72 hours, preferably for 8-48 hours, most preferably for 20-24 hours. Preferably no organic solvent is contained in or added to the reaction solution for step (a), as this is beneficial for higher conversion rate and higher yield of reaction step (a).

The intermediate product of Formula C can be isolated by dilution with water, adjusting of pH of water solution to 5-9, preferably to about 7 and optional extraction. The isolation can be accomplished by purification with column chromatography in order to characterise the obtained compound.

Accordingly, the present invention in a further aspect relates to the provision of a compound of the formula C or a salt thereof.

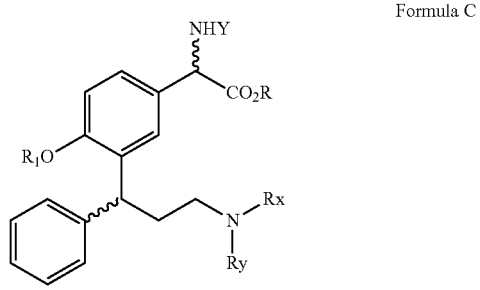

Formula C in which $R_1$ is H, $C_1$-$C_6$ alkyl, aryl substituted $C_1$-$C_2$ alkyl, $C_1$-$C_4$-alkyl substituted silyl, R is hydrogen, $C_1$-$C_6$ alkyl or aryl-$C_1$-$C_4$-alkyl and Y is hydrogen or COR', in which R' is selected from the group consisting of $C_1$-$C_4$ alkyl, $C_1$-$C_4$ alkoxy, benzyloxy, p-substituted benzyloxy and fluorenyloxy, Rx is selected from H and $C_1$-$C_3$ alkyl; and Ry is selected from $C_1$-$C_3$ alkyl (preferably $R_1$ is hydrogen, Rx and Ry is isopropyl, Formula C').

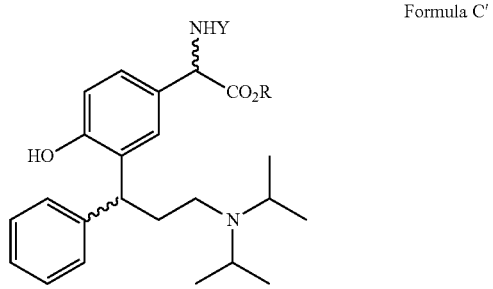

Formula C'

HFG (formula C', R, Y is H) as a most preferable molecule of the invention may be formed even from more general starting compounds of formula A' (R and Y different from H) by spontaneous cleavage of labile R and Y groups during the condensation reaction in acidic conditions. If not, the preparation of HFG could be accomplished by an additional reaction of R and Y group cleavage, routine for a skilled person. The compound of formula C is thus useful in a process of preparing a medicament, especially for preparing an anticholinergic agent for treatment of urinary incontinence or overactive bladder. A preferred use of the compound HFG is for preparing hydroxytolterodine, tolterodine or fesoterodine, optionally as an enantiomeric pure form and further optionally in a salt form.

In a preferred embodiment of the invention, isolation of the intermediate product HFG is not necessary and is dispensed with. In this embodiment, HFG can be provided in a solution, optionally in a reaction solution or any worked-up solution, to be eventually used as useful intermediate for further purposes such as subsequent reaction steps.

In a further processing without isolation of HFG, after an adjustment of pH to 5-9, preferably to about 7, a water immiscible solvent, selected from ethers or esters, preferably acetic esters is added and the intermediate is further submitted to reagents which convert it to aldehyde PHB.

Oxidative decarboxylation of the compound C or C', specifically of HFG, can be carried out simultaneously with, but preferably is carried out following, the formation of the respective compound C, C' or, specifically HFG. More specifically, transformation of amino acid compound HFG to aldehyde PHB is mechanistically three-step reaction. In the first step the amino group is oxidized to imino compound by treatment by an oxidant. The imino intermediate spontaneously hydrolyses in aqueous medium to α-keto acid which further decarboxylates at elevated temperature to the titled aldehyde.

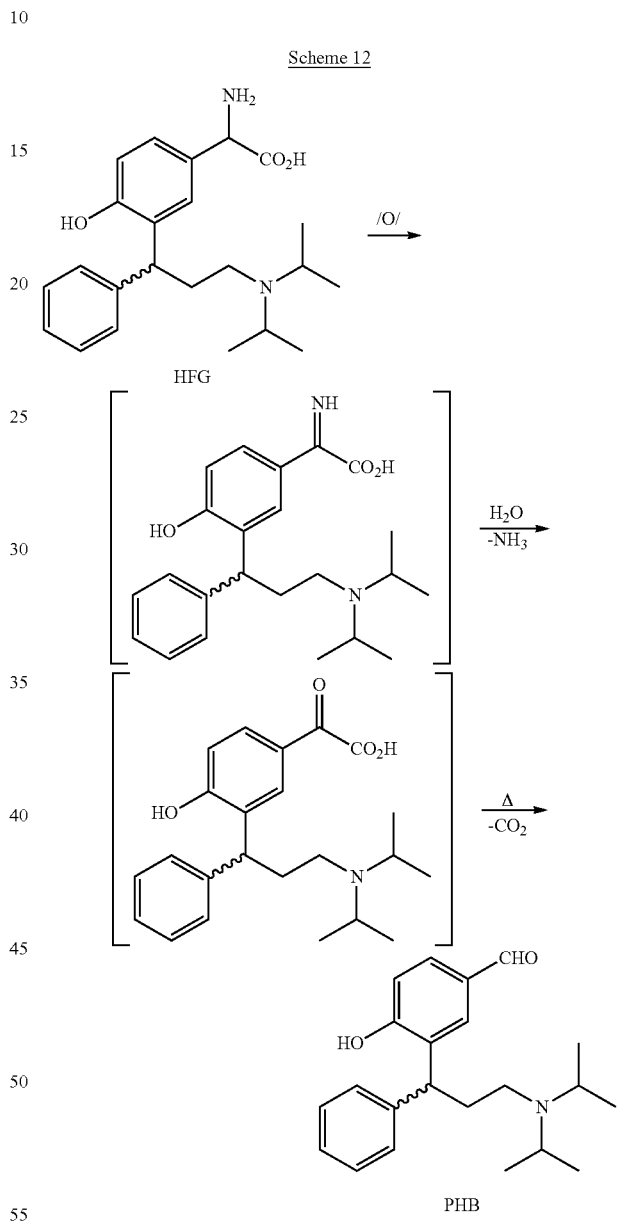

Scheme 12

Despite a complicated mechanism the conversation of cinnamyl amine DIPCA via four mechanistic steps in special conditions of invention surprisingly gives more than 50% total conversion to aldehyde PHB.

Though only HFG is shown in reaction scheme 12 as an exemplified compound of formula C in which $R_1$, Y and R respectively are H, and Rx and Ry are isopropyl, other compounds with different $R_1$, Rx and Ry substituents as indicated can be analogously used.

In one embodiment of invention the oxidation/deamination step is carried out by transamination reagents selected from reactive aldehydes and ketones selected from sugars (preferably aldoses, such as glucose), quinones (such as benzoquinone), preferably transamination reagents are selected from α-keto substituted carbonyl compounds, more preferably from their $C_2$-$C_3$ analogues, such as glyoxalic and pyruvic acids, salts, esters and aldehyde, most preferably from methylglyoxal.

In another embodiment of invention the oxidation is performed by air oxygen in the presence of catalytic amounts of radical catalysts, selected from organic compounds such as ascorbic acid or isatin or by transition metal cations, preferably selected from copper (II) salts. The introduction of oxygen is accomplished by vigorous stirring in atmospheric environment, optionally when larger volumes are used the introduction is done by blowing of air or oxygen directly into the reaction medium.

In another embodiment the amino acid is oxidized by inorganic oxidants selected form salts which include metal cations in higher oxidation states (i.e. typically using a metal cation, (which naturally occurs in different lower and higher oxidation states), in its relatively high oxidation state), such as $Fe^{3+}$ or highly oxidized anions (i.e. typically using an anion, (which naturally occurs in different lower and higher oxidation states), in its relatively high oxidation states), such as nitrites and persulfates. The most preferred option is the use of inorganic persulfates, preferably selected from alkali metal peroxodisulfates or, using peroxodisulfate species prepared in situ from corresponding sulfuric salts and hydrogen peroxide. Preferably potassium peroxodisulfate or sodium peroxodisulfate are used. Contrary to keto oxidants inorganic oxidants are not converted to organic by-products during oxidation process which is beneficial for purification process. Inorganic residues are simply washed by water and losses of product during purification are not higher than 10-15% of yield in this case.

Reaction of oxidative deamination/decarboxylation can be carried out at room temperature and above, preferably is carried out at 60° C. and above, more preferably at reflux temperature (about 100° C. such as up to 105° C.), respectively for 0.5 to 24 hours, preferably 2-10 hours. After cooling the phases are separated and the product is isolated and purified by conventional methods. This can be illustrated by one but not limited example, in which the organic phase is extracted with hydrochloric acid solution, the water phase is alkalised to pH above 7 and the product is reextracted by a water immiscible solvent or mixture of solvents optionally followed by column chromatography purification. Therefore, the formyl intermediate PHB is prepared from cheap hydroxyphenylglycine derivatives and DIPCA in one-pot procedure not using Grignard and hydride reagents. Furthermore, no protection of phenolic group is needed for this conversion.

In principle, the oxidative decarboxylation of amino acids to the aldehydes is known to the person skilled in the art and is for example described in Ganesa et al. (J. Org. Chem. vol. 50, 1985; p. 1206-1212).

PHB can then be further converted to a desired compound, notably an anticholinergic compound, by appropriate synthetic steps.

In one embodiment, PHB can be converted to hydroxytolterodine by reduction, preferably by using aluminumhydide or borohydride as reducing agent and more preferably with sodium borohydride in an alcohol such as methanol, and the product can be isolated by conventional methods, as can be depicted from scheme 11 (step from upper right to lower right side). HT as prepared by the process of the invention is typically and mostly racemic. However using chiral compound of formula A, such as chiral (R) or (S) hydroxyphenylglycine, a slight enantiomeric excess could be achieved, typically of at most 20%. Using such racemic HT or HT having such enantiomeric excess, separation of (R) enantiomer can be accomplished by crystallization with a chiral organic acid, preferably with (R)-2-acetoxy(phenyl)acetic acid, wherein (R)-HT is isolated from the precipitated diastereoisometric salt after alkalisation in highly enriched assay, as described in WO 07/138,440. Alternatively and optionally, enantiomers can be separated by chiral column chromatography or by any other enantiomer separation method known by a skilled person.

HT, preferably its enantiomeric form (R)-HT can be isolated in a solid state as a neutral molecule, or can be converted to a pharmaceutically acceptable salt. A preferred salt is mandelate. Furthermore, (R)-HT can be converted to a prodrug molecule by acylation of phenolic hydroxy group by reactive derivatives of alkanoic acids, preferably it can be acylated by isobutyryl chloride or anhydride to an isobutyrylated prodrug. Preferably, fesoterodine is converted into a salt thereof, preferably fumarate salt.

A preferred embodiment of making fesoterodine or a salt thereof (illustrated by its fumarate salt) can be depicted from scheme 13 below. This synthesis scheme, starting from PHB or HT, involves only 3 or 2 steps, respectively to obtain fesoterodine.

Scheme 13

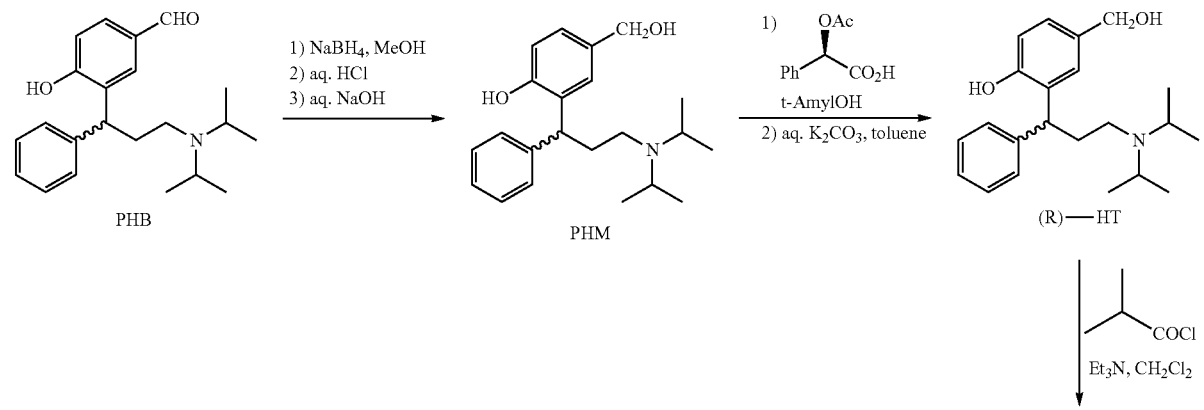

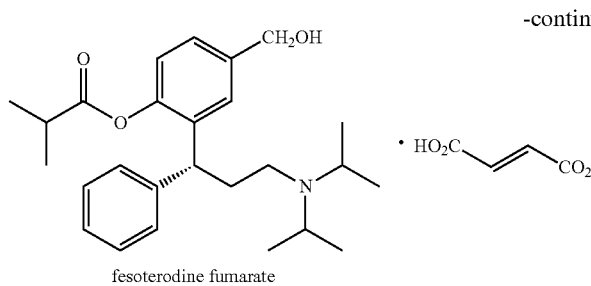

fesoterodine fumarate

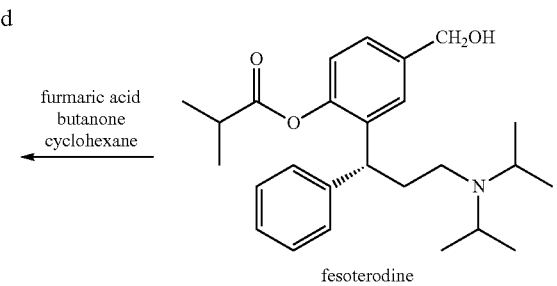

fesoterodine

The present invention in a further aspect relates to the preparation of a compound of Formula G or a salt thereof.

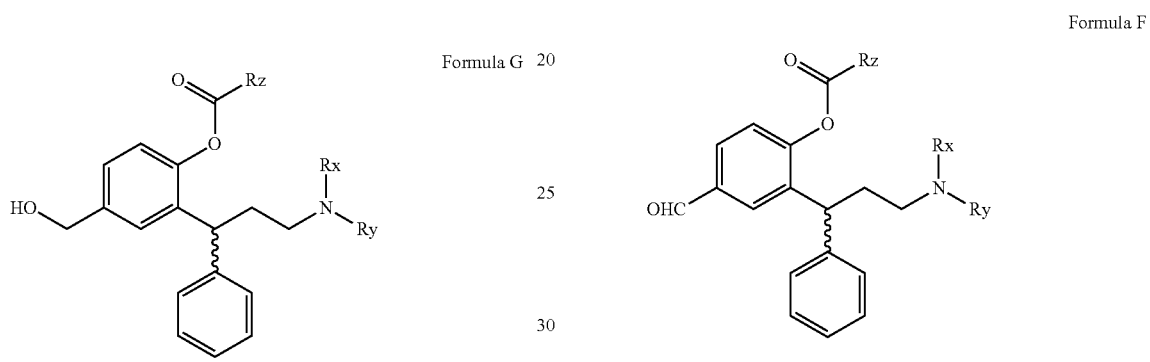

Formula G wherein Rx is selected from H and $C_1$-$C_3$ alkyl; Ry is selected from $C_1$-$C_3$ alkyl, and Rz is selected from H, $C_1$-$C_8$-alkyl or phenyl
comprising
acylation of compound of formula D'

Formula D' wherein Rx and Ry are same as above,
with a compound of formula RzCOX,
wherein Rz is same as above and wherein X is a leaving group selected from halogen selected from Cl, Br or I,
OCORq, wherein Rq is selected from $C_1$ to $C_6$ halogenated alkyl or is same as Rz,
O$SO_2$Rw, wherein Rw is selected from $C_1$-$C_6$ alkyl, $C_1$-$C_6$ substituted alkyl, phenyl or substituted phenyl, preferably X is Cl or OCOiPr
to give an intermediate of Formula F Formula F wherein Rx, Ry and Rz are the same as above
followed by selective reduction of formyl group, preferably by borohydrides to give the compound of formula G.

In a preferred embodiment Rx, Ry and Rz are isopropyl. Fesoterodine (formula G; Rx, Ry and Rz are isopropyl) is prepared as shown in Scheme 14, wherein compounds of any of the steps are optionally separated to enantiomers, preferably isolating the (R)-enantiomer, by selective precipitation of diasteroisomeric salts with chiral acids or by chiral column chromatography.

Scheme 14

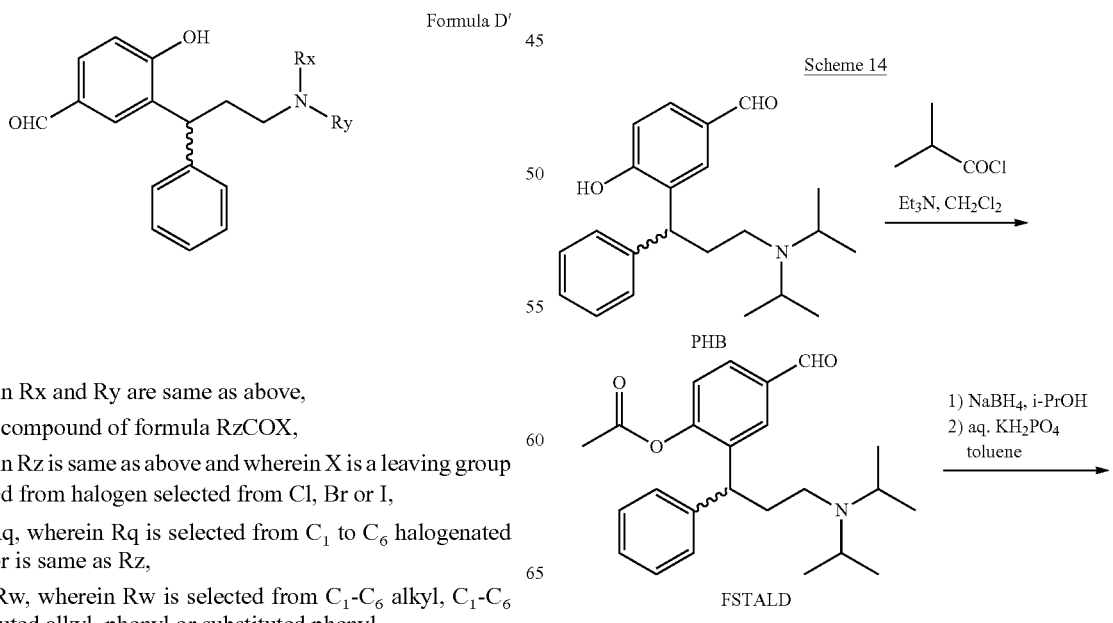

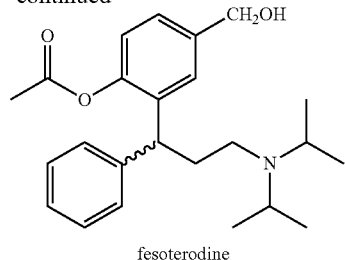

fesoterodine

Accordingly, the present invention in a further aspect relates to the compound of Formula F

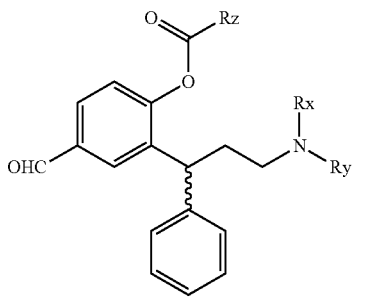

Formula F wherein Rx is selected from H and $C_1$-$C_3$ alkyl; Ry is selected from $C_1$-$C_3$ alkyl and Rz is selected from H, $C_1$-$C_8$-alkyl or phenyl.

FSTALD (formula F', Rx, Ry and Rz are isopropyl) is the most preferable molecule of the invention. The compound of formula F is useful in a process of preparing a medicament, especially for preparing an anticholinergic agent for treatment of urinary incontinence or overactive bladder. A preferred use of the compound FSTALD is for preparing hydroxytolterodine, tolterodine or fesoterodine, optionally as an enantiomeric pure form and further optionally in a salt form.

HT, or salts of HT or fesoterodine can be used as an anticholinergic for treatment of diseases linked to muscarinic acceptor inhibition, such for the treatment of urinary incontinence or overactive bladder. Accordingly, tolterodine, HT or fesoterodine or any salts thereof is obtained as disclosed herein and subsequently formulated as an active pharmaceutical ingredient with a pharmaceutically acceptable carrier, known to those skilled in the art, to prepare a pharmaceutical composition for example in form of tablet, capsules, pellets, granules and suppositories or their combined forms. An amount of the anticholinergic agent, notably of tolterodine, HT or fesoterodine or any salts thereof as the aforementioned active pharmaceutical ingredient, is suitable chosen to effect muscarinic acceptor inhibition and in particular to be effective for the treatment of urinary incontinence or overactive bladder. Pharmaceutical composition in accordance with present invention can be suitable for immediate release or modified release of tolterodine, HT or fesoterodine or any salts thereof obtained as disclosed herein. Solid pharmaceutical compositions can be for example coated with aim of increasing peletibility or regulating the disintegration or absorption.

Pharmaceutically acceptable excipients may be selected from the group consisting of binders, diluents, disintegrating agents, stabilizing agents, preservatives, lubricants, fragrances, flavoring agents, sweeteners and other excipients known in the field of the pharmaceutical technology. Preferably, carriers and excipients may be selected from the group consisting of lactose, microcrystalline cellulose, cellulose derivatives, (e.g. hydroxypropylcellulose, croscarmellose sodium), polyacrylates, calcium carbonate, starch, colloidal silicone dioxide, sodium starch glycolate, talc, magnesium stearate, mannitol, polyvinylpyrrolidone, polyethylene glycol and other excipients known in the field of the pharmaceutical technology.

Experimental Procedures

Example 1

Preparation of N,N-diisopropyl-3-phenylprop-2-en-1-amine (DIPCA)

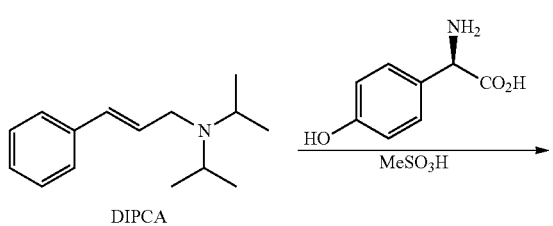

DIPCA

The title compound was prepared using the method described in WO 2007/147547.

A mixture of cinnamyl chloride (905 mL, 6.5 mol), diisopropylamine (1.37 L, 9.75 mol), potassium carbonate (0.90 kg, 6.5 mol), potassium iodide (54 g, 0.325 mol), toluene (2.1 L) and methanol (0.50 L) was stirred at reflux temperature for 20 hours. The mixture was cooled to 25° C. and water (5.2 L) was added. Phases were separated and the organic phase was extracted with brine. Organic phase was concentrated under reduced pressure (50° C.) and then water (10.4 L) and toluene (2.6 L) were added and the pH was adjusted to 2 by addition of concentrated hydrochloric acid (~500 mL). The resulting mixture was stirred for 15 minutes and the phases were separated. The aqueous phase was re-extracted twice with toluene (2×2.6 L). Then the pH of the aqueous phase was adjusted to 12 by addition of 8 M aqueous sodium hydroxide solution (750 mL). To the resulting white suspension was added heptane (5.2 L) and the mixture was stirred for 15 minutes. Phases were separated and aqueous phase was re-extracted twice with heptane (2×2.6 L). Combined organic phases were dried over $Na_2SO_4$ and concentrated to give 1.32 kg (93% yield) of DIPCA.

Example 2

Preparation of 2-amino-2-(3-(3-(diisopropylamino)-1-phenylpropyl)-4-hydroxyphenyl)acetic acid (HFG)

-continued

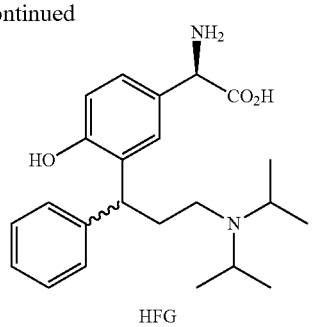

HFG

A mixture of DIPCA (10.9 g, 50 mmol), (R)-2-amino-2-(4-hydroxyphenyl)acetic acid (10.0 g, 60 mmol) and methanesulfonic acid (26 mL, 0.40 mol) was stirred at 120° C. for 20 hours. The solution was cooled down and water (50 mL) was added. Then the pH of the solution was adjusted to 7 by addition of 8 M aqueous sodium hydroxide (~45 mL) and water was added so that the final volume was 150 mL. A 3 mL aliquot of this solution was taken and subjected to chromatography (Biotage C18HS 25+M column; elution with 10 mM aqueous $NaH_2PO_4$:acetonitrile 100:0→0:100) to give 370 mg (96% yield) of HFG as colourless solid (mixture of diastereoisomers). $^1$H NMR ($D_2O$): δ 0.99 (m, 12H), 2.28 (m, 2H), 2.66-2.87 (m, 2H), 3.37 (m, 2H), 4.17 (m, 1H), 4.51 (2 s, 1H), 6.71 (m, 1H), 6.95-7.09 (m, 2H), 7.11-7.22 (m, 5H). $^{13}$C NMR ($D_2O$): δ 18.66, 18.72, 20.4, 20.5, 34.56, 34.63, 43.8, 44.2, 48.9, 49.0, 57.8, 60.67, 60.74, 119.0, 119.1, 128.86, 128.89, 129.5, 129.7, 130.1, 130.5, 130.6, 130.7, 131.3, 131.60, 131.62, 133.3, 133.4, 145.1, 145.3, 156.96, 157.03, 176.0, 176.2.

Comparative Example 3

Attempt of preparation of 3-(3-(diisopropylamino)-1-phenylpropyl)-4-hydroxybenzaldehyde (PHB) from 4-hydroxybenzaldehyde

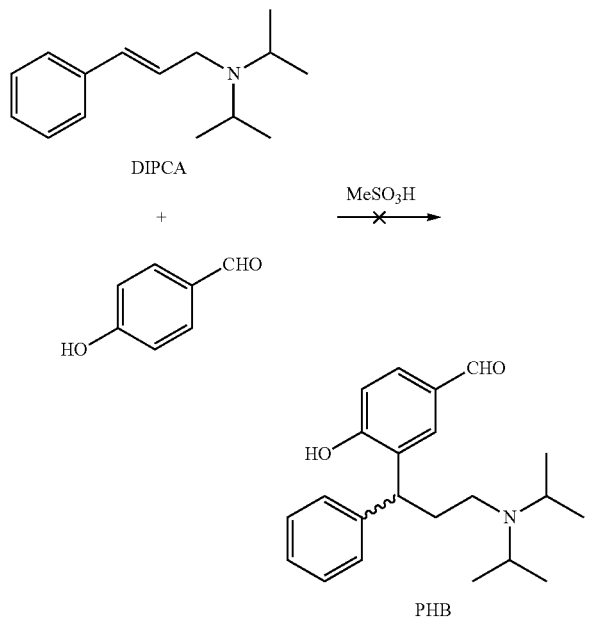

A mixture of DIPCA (1.09 g, 5 mmol), 4-hydroxybenzaldehyde (2.44 g, 20 mmol) and methanesulfonic acid (1.2 mL, 18 mol) was stirred at 100° C. for 3 hours. During this time the reaction mixture solidifies in a form of rubbery gel. The mixture was cooled to room temperature and left standing for 16 hours. HPLC analysis reveals 95 area % of 4-hydroxybenzaldehyde, 3 area % of DIPCA, and more than 15 minor products.

Example 4

Reaction of preparation of 3-(3-(diisopropylamino)-1-phenylpropyl)-4-hydroxybenzaldehyde (PHB) from DIPCA in one pot process

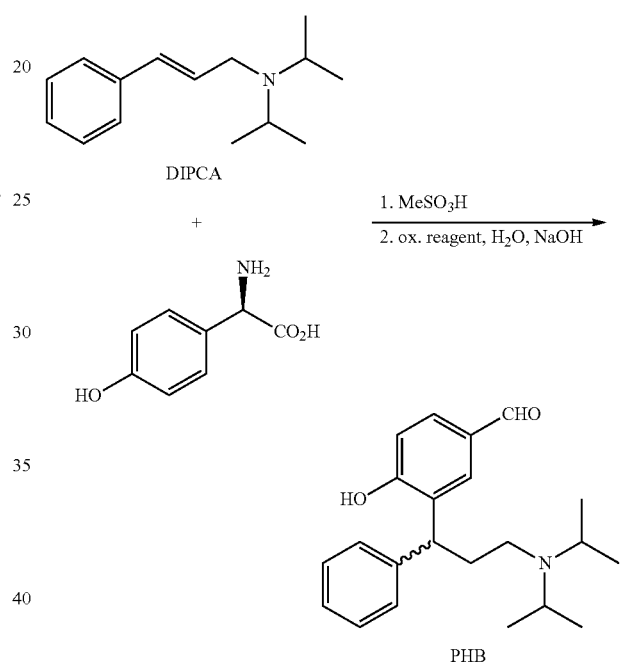

A mixture of DIPCA (10.9 g, 50 mmol), (R)-2-amino-2-(4-hydroxyphenyl)acetic acid (10.0 g, 60 mmol) and methanesulfonic acid (26 mL, 0.40 mol) was stirred at 120° C. for 20 hours. The solution was cooled down and water (50 mL) was added. Then the pH of the solution was adjusted to 7 by addition of 8 M aqueous sodium hydroxide (~45 mL) and water was added so that the final volume was 150 mL. A 3 mL aliquot of this solution was taken and diluted with water (see table below[a]). To this solution was added selected reagent and catalyst if necessary[b] (see table below) and the mixture was stirred at selected temperature[c]. After the time indicated in the table below[d] a sample was taken and subjected to HPLC analysis. Results are summarised in table below.

| Entry | Reagent/Cat.[b] | Reagent [mmol] | Added water [mL][a] | Temp. [° C.][c] | Time [h][d] | HPLC Yield [Area %] |
|---|---|---|---|---|---|---|
| 1 | Glucose | 2 | 25 | 100 | 21 | 20 |
| 2 | Benzoquinone | 1.2 | 25 | 100 | 18 | 42 |
| 3 | Sodium pyruvate | 1 | 5 | 100 | 19 | 46 |

-continued

| Entry | Reagent/Cat.[b] | Reagent [mmol] | Added water [mL][a] | Temp. [° C.][c] | Time [h][d] | HPLC Yield [Area %] |
|---|---|---|---|---|---|---|
| 4 | Pyruvic acid. | 2.4 | 25 | 100 | 22 | 32 |
| 5 | Glyoxal | 1.2 | 25 | 100 | 4 | 39 |
| 6 | Methylglyoxal | 1 | 25 | 100 | 21 | 52 |
| 7 | Glyoxylic acid | 1.2 | 25 | 100 | 22 | 29 |
| 8 | Air/Cu(OAc)$_2$ | 0.1[b] | 5 | 100 | 18 | 42 |
| 9 | Air/isatin | 0.1[b] | 25 | 100 | 4 | 41 |
| 10 | Air/ascorbic acid-Cu(OAc)$_2$ | 2/0.04[b] | 2 | 80 | 19 | 7 |
| 11 | Fe$_2$(SO$_4$)$_3$ | 1.5 | 25 | 100 | 22 | 38 |
| 10 | K$_2$S$_2$O$_8$ | 1 | 25 | 100 | 4 | 54 |

Example 5

Preparation of 3-(3-(diisopropylamino)-1-phenylpropyl)-4-hydroxybenzaldehyde (PHB)

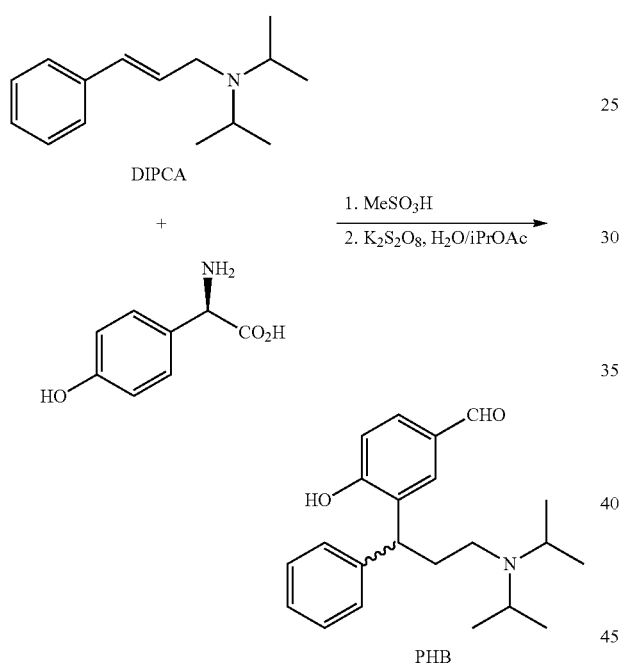

A mixture of DIPCA (10.9 g, 50 mmol), (R)-2-amino-2-(4-hydroxyphenyl)acetic acid (10.0 g, 60 mmol) and methanesulfonic acid (26 mL, 0.40 mol) was stirred at 130° C. for 23 hours. The solution was cooled down and water (250 mL) was added. The pH of the solution was adjusted to 7 by addition of 8 M aqueous sodium hydroxide (~45 mL). To the solution were added water (200 mL), isopropyl acetate (200 mL) and potassium peroxodisulfate (18.9 g, 70 mmol) and the mixture was stirred at reflux temperature (78° C.) for 4 hours. The mixture was cooled to 25° C. and the phases were separated. Organic phase was extracted with 10 mM aqueous hydrochloric acid (100 mL). Aqueous phases were combined and pH was adjusted to 9 by addition 8 M aqueous sodium hydroxide. The mixture was extracted four times with dichloromethane:methanol (8:2) mixture (4×300 mL). After concentration the product was purified by chromatography (silica gel; elution with dichloromethane:methanol=10:1) to give 6.33 g (37% yield) of PHB. $^1$H NMR (CDCl$_3$): δ 1.11 (d, 6H, J=6.5 Hz), 1.18 (d, 6H, J=6.6 Hz), 2.16 (m, 1H), 2.42 (m, 2H), 2.78 (m, 1H), 3.34 (hept, 2H, J=6.6 Hz), 4.53 (dd, 1H, J=4.5 Hz, J=11.0 Hz), 6.84 (d, 1H, J=8.4 Hz), 7.07 (br s, 1H), 7.14-7.31 (m, 5H), 7.52 (m, 1H), 9.55 (s, 1H). $^{13}$C NMR (CDCl$_3$): δ 18.8, 19.3, 32.6, 39.5, 42.6, 49.4, 118.8, 126.4, 126.8, 128.3, 128.4, 130.7, 130.8, 132.8, 143.7, 166.8, 190.7.

Example 6

Preparation of 3-(3-(diisopropylamino)-1-phenylpropyl)-4-hydroxybenzaldehyde (PHB)

A mixture of DIPCA (10.9 g, 50 mmol), (R)-2-amino-2-(4-hydroxyphenyl)acetic acid (10.0 g, 60 mmol) and 70% sulfuric acid (19 g) was stirred at 105° C. for 44 hours. The mixture was cooled down and water (250 mL) was added. The pH of the solution was adjusted to 8 by addition of 8 M aqueous sodium hydroxide (~50 mL). To the solution were added water (200 mL), isopropyl acetate (200 mL) and sodium peroxodisulfate (19.0 g, 80 mmol) and the mixture was stirred at reflux temperature (76° C.) for 4 hours. The mixture was cooled to 25° C. and the phases were separated. Organic phase was extracted twice with 10 mM aqueous hydrochloric acid (2×50 mL). Aqueous phases were combined and pH was adjusted to 9 by addition 8 M aqueous sodium hydroxide. The mixture was extracted four times with dichloromethane/methanol (8:2) mixture (4×300 mL). After concentration the product was purified by chromatography (silica gel; elution with dichloromethane:methanol=10:1) to give 5.19 g (31% yield) of PHB.

Example 7

Preparation of 3-(3-(diisopropylamino)-1-phenylpropyl)-4-hydroxybenzaldehyde (PHB)

The procedure according to Example 6 was followed, but using DIPCA (10.9 g, 50 mmol) and (S)-2-amino-2-(4-hydroxyphenyl)acetic acid (10.0 g, 60 mmol). Yield of PHB: 5.6 g (33%).

Example 8

Preparation of 3-(3-(diisopropylamino)-1-phenylpropyl)-4-hydroxybenzaldehyde (PHB)

The procedure according to Example 6 was followed, but using DIPCA (10.9 g, 50 mmol) and racemic 2-amino-2-(4-hydroxyphenyl)acetic acid (10.0 g, 60 mmol). Yield of PHB: 3.9 g (25%).

Example 9

Preparation of 2-(3-(diisopropylamino)-1-phenylpropyl)-4-(hydroxymethyl)phenol

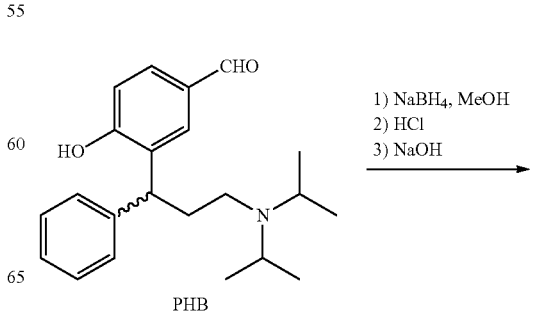

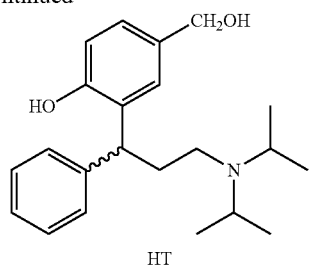

The title compound was prepared using the method described in WO 2007/147547.

A solution of PHB (6.33 g, 18.6 mmol) in methanol (40 mL) was cooled to 0° C. To the cooled solution was added sodium borohydride in portions and the solution was stirred for 2 hours. The solution was concentrated under reduced pressure and dichloromethane (50 mL) and 1M aqueous hydrochloric acid were added (30 mL). The mixture was stirred for 5 min and the pH was adjusted to 8 using 1 M aqueous sodium hydroxide. The phases were separated and the aqueous phase was re-extracted four times with dichloromethane (4×30 mL). The combined organic phases were concentrated and the product was purified by chromatography (silica gel; dichloromethane:methanol=1:1) to give 5.44 g (86% yield) of HT. $^1$H NMR (CDCl$_3$): δ 1.09 (d, 6H, J=6.7 Hz), 1.15 (d, 6H, J=6.7 Hz), 2.10 (m, 1H), 2.37 (m, 2H), 2.74 (m, 1H), 3.25 (hept, 2H, J=6.7 Hz), 4.42 (s, 2H), 4.52 (dd, 1H, J=3.5 Hz, J=11.0 Hz), 6.74 (d, 1H, J=2.1 Hz), 6.90 (d, 1H, J=8.2 Hz), 7.06 (dd, 1H, J=2.1 Hz, J=8.2 Hz), 7.19-7.36 (m, 5H). $^{13}$C NMR (CDCl$_3$): δ 19.5, 19.9, 33.1, 39.4, 41.9, 47.9, 65.3, 118.5, 126.2, 126.5, 127.5, 128.3, 128.5, 132.5, 132.8, 144.4, 155.5.

Example 10

Preparation of (R)-2-(3-(diisopropylamino)-1-phenylpropyl)-4-(hydroxymethyl)phenol ((R)-HT)

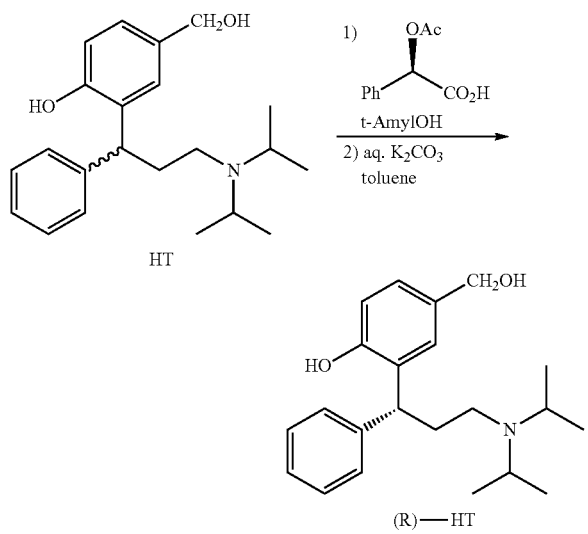

A solution of HT (5.12 g, 15 mmol) in t-amyl alcohol (82 mL) was heated to 70° C. and a solution of (R)-acetoxy(phenyl)acetic acid (1.36 g, 7 mmol) in t-amyl alcohol (20 mL) was added over one hour. The resulting mixture was gradually cooled to 25° C. and stirred overnight. The resulting slurry was filtered and the cake was washed twice with t-amyl alcohol (2×20 mL). The white solid was dried under reduced pressure at 40° C. to give 3.17 g (85% yield) of (R)-2-(3-(diisopropylamino)-1-phenylpropyl)-4-(hydroxymethyl)phenol (R)-acetoxy(phenyl)acetate.

Part of this salt (2.16 g, 4.0 mmol) was suspended in toluene (22 mL), heated to 50° C. and 8% aqueous solution of potassium carbonate (25 mL) was added. The resulting mixture was stirred vigorously at 50° C. for 1 hour and the phases were separated. The organic phase was washed with water (4 mL) and concentrated under reduced pressure to give 1.3 g (81% yield) of (R)-HT.

Example 11

Preparation of (R)-2-(3-(diisopropylamino)-1-phenylpropyl)-4-(hydroxymethyl)phenol(S)-mandelate ((R)-HT (S)-MA)

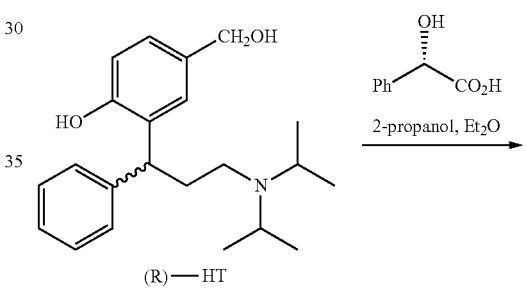

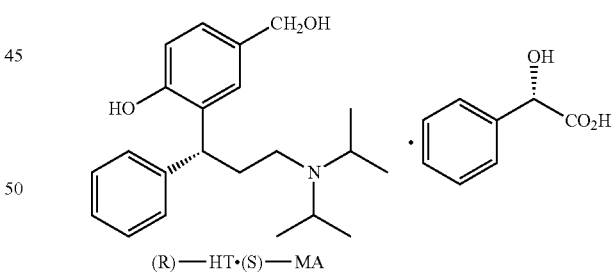

To a solution of (R)-HT (1.11 g, 3.25 mmol) in 2-propanol a solution of (S)-mandelic acid (0.48 g, 3.0 mmol) in 2-propanol was added. Dry diethyl ether (2.5 g) was added and the resulting solution was stirred for 2 hours at 25° C. The resulting white precipitate was filtered off, washed twice with a of 2-propanol/diethyl ether (1:1) mixture (2×5 mL) and dried under reduced pressure at 40° C. to give 1.39 g (94% yield) of (R)-2-(3-(diisopropylamino)-1-phenylpropyl)-4-(hydroxymethyl)phenol (S)-mandelate.

Example 12

Preparation of 2-[3-(N,N-diisopropylamino)-1(R)-phenylpropyl]-4-(hydroxymethyl)phenyl 2-methyl-propionate hydrofumaric salt

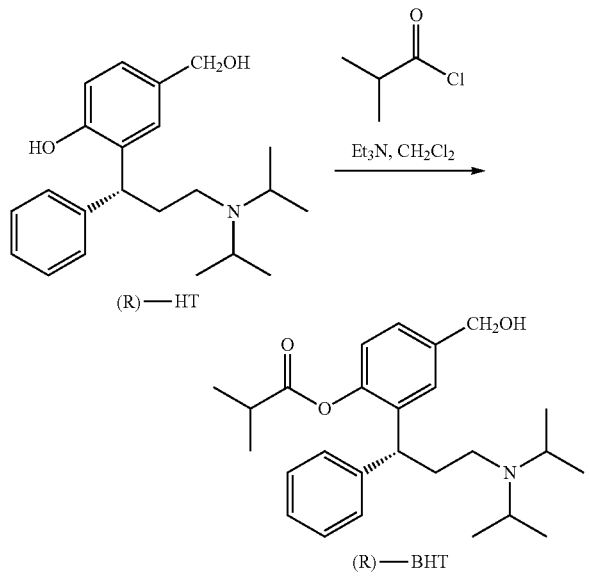

A solution of (R)-HT (0.85 g, 2.5 mmol) and triethylamine (0.37 mL, 2.65 mmol) in dichloromethane (10 mL) was cooled to 0° C. and a solution of isobutyryl chloride (0.28 mL, 2.5 mmol) in dichloromethane was added dropwise. The solution was stirred for 15 minutes at 0° C. and for 30 minutes at 25° C. Water (4 mL) was added and the phases were separated. The organic phase was washed with 5% aqueous sodium hydrogen carbonate (4 mL) and concentrated under reduced pressure to give 0.99 g (96% yield) of isobutyrylated product (R)-BHT.

A solution of the previously prepared intermediate (0.84 g, 2.04 mmol) in 2-butanone (1.8 mL) was heated to 50° C. and fumaric acid (0.24 g, 2.04 mmol) was added. Stirring was continued for 10 min and cyclohexane (0.4 mL) was added. The mixture was stirred for 18 hours at 25° C. and for 3 hours at 0° C. The resulting slurry was filtered and the solid was washed with cyclohexane/2-butanone (1 mL; 9:1 v/v) mixture. The solid was dried under reduced pressure at 30° C. to give 0.86 g (80% yield) of the titled compound.

Example 13

Preparation of 2-(3-(diisopropylamino)-1-phenylpropyl)-4-formylphenyl isobutyrate (FSTALD)

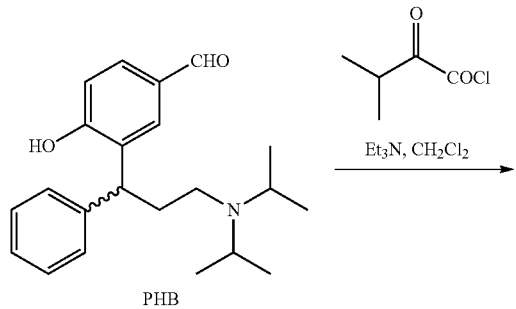

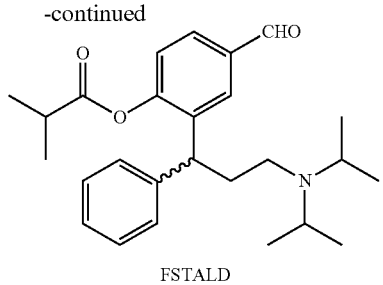

To a cold (−15° C.) solution of PHB (9.0 g, 26.6 mmol) in dichloromethane (105 mL) was added triethylamine (4.43 mL, 32 mmol) and a solution of isobutyryl chloride (3.2 mL, 29 mmol) in dichloromethane (32 mL) was added dropwise over a period of 10 min. The solution was stirred for 20 minutes at 0° C. and for 60 minutes at 20-25° C. Water (40 mL) was added and the phases were separated. The organic phase was washed with 5% aqueous sodium hydrogen carbonate (40 ml), dried with sodium sulphate, filtered and concentrated under reduced pressure to give 10.8 g (100% yield) of 2-(3-(diisopropylamino)-1-phenylpropyl)-4-formylphenyl isobutyrate (FSTALD). $^1$H NMR (CDCl$_3$): δ 0.92 (m, 12H), 1.29 (d, 3H, J=7.1 Hz), 1.34 (d, 3H, J=7.0 Hz), 2.19 (m, 2H), 2.37 (m, 2H), 2.82 (m, 1H), 2.99 (m, 2H), 4.23 (t, 1H, J=7.7 Hz), 7.15-7.29 (m, 6H), 7.75 (dd, 1H, J=2.0 Hz, J=8.2 Hz), 7.93 (d, 1H, J=1.8 Hz), 9.96 (s, 1H).

Example 14

Preparation of 2-(3-(diisopropylamino)-1-phenylpropyl)-4-(hydroxymethyl)phenyl isobutyrate

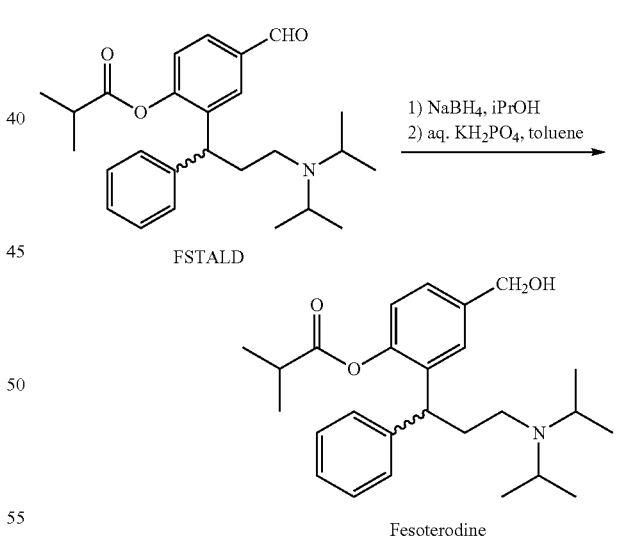

To a cold (0° C.) solution of FSTALD (2.05 g, 5 mmol) in 2-propanol (20 mL) was added sodium borohydride (284 mg, 7.5 mmol) and the resulting mixture was stirred at 0° C. for 3 hours. Toluene (50 mL) was added, followed by saturated aqueous potassium dihydrogen phosphate solution (10 mL). The phases were separated and the organic phase was washed twice with water (2×10 mL) and then with brine (10 mL). The organic phase was dried with sodium sulphate, filtered and concentrated to afford 1.90 g (92% yield) of fesoterodine as oil.

Comparative Example

WO 2007/147547, Example 12

Preparation of 3-(3-(diisopropylamino)-1-phenylpropyl)-4-hydroxybenzaldehyde (PHB): 2.04 g of N,N-diisopropyl-3-phenylprop-2-en-1-amine was added to 4.76 g of p-hydroxybenzaldehyde and 3.1 g of methanesulfonic acid and heated to 130° C. for 23 hours. Solid mass was obtained. The flask was broken and the resulting solid was broken down in a mortar. To the powdered mass was added water (40 mL) and toluene (400 mL) and the pH was adjusted to 9.5 with $Na_2CO_3$. The toluene layer was isolated and washed with water (40 mL). Concentration of toluene phase yielded 150 mg of oily mass (with some solid substance).

HPLC of this residue revealed no 3-(3-(diisopropylamino)-1-phenylpropyl)-4-hydroxybenzaldehyde (PHB).

The invention claimed is:

1. A process of preparing fesoterodine or a salt thereof, comprising the steps of:
    (a) reacting N,N-diisopropyl-3-phenylprop-2-en-1-amine with hydroxyphenylglycine or a derivative thereof denoted by formula A'

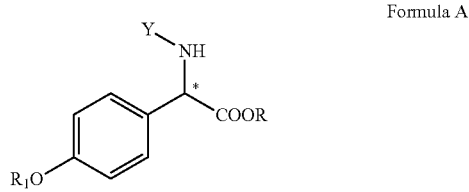

Formula A in which * denotes chiral C atom, R is hydrogen, $C_1$-$C_6$ alkyl or aryl-$C_1$-$C_4$-alkyl and Y is hydrogen or COR', in which R' is selected from the group consisting of $C_1$-$C_4$ alkyl, $C_1$-$C_4$ alkoxy, benzyloxy, p-substituted benzyloxy and fluorenyloxy, in the presence of an acid;
    (b) optionally removing R and Y, if other than H
    (c) followed by oxidative decarboxylation in the presence of an oxidizing reagent to obtain 3-(5-formyl-2-hydroxyphenyl)-N,N-diisopropyl-3-phenylpropylamine;
    (d) reducing the formed 3-(5-formyl-2-hydroxyphenyl)-N,N-diisopropyl-3-phenylpropylamine to obtain hydroxytolterodine (HT);
    and
    (e) carrying out acylation of the phenolic hydroxy group HT or of (R)-HT obtained in step (d) by isobutyryl chloride or isobutyric anhydride to obtain fesoterodine,
    (f) optionally converting fesoterodine into a salt thereof; or wherein steps (d)-(e) are replaced by the steps of:
    (d') carrying out acylation of the phenolic hydroxy group of 3-(5-formyl-2-hydroxyphenyl)-N,N-diisopropyl-3-phenylpropylamine obtained in step (c) by isobutyryl chloride or isobutyric anhydride,
    (e') followed by selective reduction of formyl group;
    wherein optionally any of the compounds of the steps (d)-(e) or (d')-(e') are separated into enantiomers.

2. The process according to claim 1, wherein steps (a) and (b) proceed in a one pot reaction.

3. The process according to claim 1, wherein the acid in step (a) is selected from inorganic acids and organic sulfonic acids, wherein optionally the acid is diluted with water and/or with aliphatic acid.

4. The process according to claim 1, wherein no organic solvent is contained in or added to the reaction solution for step (a).

5. The process according to claim 1, wherein before step (c), the acid reaction solution of step (a) is adjusted to a pH in the range from 5 to 9, then a water immiscible solvent is added, and then step (c) is carried out.

6. The process according to claim 1, wherein step (c) is carried out by any one of
    (i) using a transamination reagent selected from reactive aldehydes and ketones;
    (ii) using air oxygen in the presence of a radical catalyst;
    (iii) using inorganic oxidants selected from salts of metal cations in relatively high oxidation states, and anions in relatively high oxidation states.

7. The process according to claim 1, wherein oxidation in step (c) is carried out using any oxidant selected from the group of benzoquinone, glyoxalic acid and pyruvic acids and their salts and esters, inorganic persulfates, or using peroxodisulfate species prepared in situ from corresponding sulfuric salts and hydrogen peroxide.

* * * * *

UNITED STATES PATENT AND TRADEMARK OFFICE
CERTIFICATE OF CORRECTION

| | | |
|---|---|---|
| PATENT NO. | : 8,703,996 B2 | Page 1 of 1 |
| APPLICATION NO. | : 13/582947 | |
| DATED | : April 22, 2014 | |
| INVENTOR(S) | : Damjan Sterk | |

It is certified that error appears in the above-identified patent and that said Letters Patent is hereby corrected as shown below:

On the Title Page, Item (54) and in the Specification, Column 1, Lines 1-2, title

~~SHORT SYNTHESIS OF TOLTERODIN, INTERMEDIATES AND METABOLITES~~ should read as

SHORT SYNTHESIS OF TOLTERODINE INTERMEDIATES AND METABOLITES

Signed and Sealed this
Eighth Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,703,996 B2  Page 1 of 1
APPLICATION NO. : 13/582947
DATED : April 22, 2014
INVENTOR(S) : Damjan Sterk It is certified that error appears in the above-identified patent and that said Letters Patent is hereby corrected as shown below:

On the Title Page, Item (54) and in the Specification, Column 1, Lines 1-2, title should read as

SHORT SYNTHESIS OF TOLTERODINE, INTERMEDIATES AND METABOLITES

Signed and Sealed this
Twenty-fourth Day of March, 2015

Michelle K. Lee
*Director of the United States Patent and Trademark Office*